US011554200B2

(12) United States Patent
Lo et al.

(10) Patent No.: US 11,554,200 B2
(45) Date of Patent: Jan. 17, 2023

(54) GRAVITY FED DIALYSIS SYSTEMS AND METHODS

(71) Applicants: BAXTER INTERNATIONAL INC., Deerfield, IL (US); BAXTER HEALTHCARE SA, Glattpark (CH)

(72) Inventors: Ying-Cheng Lo, Long Grove, IL (US); Aaron W. Brown, Antioch, IL (US); Yuanpang Samuel Ding, Long Grove, IL (US); Ieng Kin Lao, Taipei Taipei (MO); Zachariah Louis Fuller, Appleton, WI (US); Aaron Joseph Geier, Hortonville, WI (US); Alan John Harvey, Lafayette, CO (US); Leansu Kiatoukaysy Lo, Appleton, WI (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 142 days.

(21) Appl. No.: 17/076,152

(22) Filed: Oct. 21, 2020

(65) Prior Publication Data

US 2021/0046236 A1 Feb. 18, 2021

Related U.S. Application Data

(62) Division of application No. 15/946,395, filed on Apr. 5, 2018, now Pat. No. 10,814,057.

(51) Int. Cl.
*A61M 1/28* (2006.01)
*A61M 39/10* (2006.01)
*A61M 39/28* (2006.01)

(52) U.S. Cl.
CPC .............. *A61M 1/28* (2013.01); *A61M 1/282* (2014.02); *A61M 39/105* (2013.01);
(Continued)

(58) Field of Classification Search
CPC .. G01G 17/04; A61M 1/28; A61M 2205/3393
See application file for complete search history.

(56) References Cited

U.S. PATENT DOCUMENTS 4,628,186 A * 12/1986 Bergemann ........... A61M 1/166
392/479
4,878,516 A 11/1989 Mathieu
(Continued)

FOREIGN PATENT DOCUMENTS

DE 102011018601 10/2012
DE 10 2015 010467 A1 2/2017
(Continued)

OTHER PUBLICATIONS

International Search Report and Written Opinion dated Oct. 8, 2019 in corresponding PCT Application No. PCT/US2019/025816 (21 Pages).

*Primary Examiner* — Natalie Huls
(74) *Attorney, Agent, or Firm* — K&L Gates LLP

(57) ABSTRACT

A gravity fed peritoneal dialysis ("PD") machine includes: a frame configured to be set on a supporting surface; at least one load cell; a scale platform supported by the frame via the at least one load cell positioned between the frame and the scale platform; a drain container support in mechanical communication with and extending downwardly from the scale platform, the machine configured such that when the frame is set on the supporting surface, at least one fresh PD fluid supply container is supportable by the scale platform above the at least one load cell and at least one used PD fluid drain container is supportable by the drain container support below the at least one load cell, so that a combined weight of fresh PD fluid and used PD fluid may be sensed by the at least one load cell.

19 Claims, 13 Drawing Sheets

(52) U.S. Cl.
CPC ..... *A61M 39/28* (2013.01); *A61M 2205/3337* (2013.01); *A61M 2205/3368* (2013.01); *A61M 2205/3393* (2013.01); *A61M 2205/3653* (2013.01); *A61M 2205/505* (2013.01); *A61M 2205/7536* (2013.01); *A61M 2209/084* (2013.01)

(56) References Cited

U.S. PATENT DOCUMENTS

| | | |
|---|---|---|
| 4,899,903 A | 2/1990 | Miyasaka |
| 5,045,067 A | 9/1991 | Ohnaka |
| 5,053,003 A | 10/1991 | Dadson |
| 5,057,074 A | 10/1991 | Suzuki |
| 5,221,267 A | 6/1993 | Folden |
| 5,250,041 A | 10/1993 | Folden |
| 5,259,843 A | 11/1993 | Watanabe |
| 5,336,173 A | 8/1994 | Folden |
| 5,338,293 A | 8/1994 | Jeppsson |
| 5,445,610 A * | 8/1995 | Evert ............ A61M 1/28 604/29 |
| 5,693,008 A | 12/1997 | Brugger |
| 5,836,619 A | 11/1998 | Shemesh |
| 6,322,551 B1 | 11/2001 | Brugger |
| 6,739,628 B2 | 5/2004 | Kanner |
| 7,452,346 B2 | 11/2008 | Axelsson |
| D850,959 S | 6/2019 | Zeyher |
| D851,257 S | 6/2019 | Zeyher et al. |
| 10,603,424 B2 | 3/2020 | Burbank |
| 2005/0126998 A1 | 6/2005 | Childers et al. |
| 2007/0276328 A1 | 11/2007 | Childers et al. |
| 2009/0299273 A1* | 12/2009 | Lee ............ A61M 1/28 604/29 |
| 2009/0312694 A1* | 12/2009 | Bedingfield ............ A61M 1/28 210/175 |
| 2012/0267290 A1* | 10/2012 | Hochrein ............ A61M 1/3644 210/85 |
| 2016/0216150 A1* | 7/2016 | Groeber ............ A61M 1/28 |
| 2018/0236153 A1* | 8/2018 | Zeyher ............ A61M 1/28 |
| 2018/0236154 A1 | 8/2018 | Zeyher |
| 2018/0236155 A1 | 8/2018 | Wieskotten et al. |
| 2019/0376835 A1 | 12/2019 | Hassler et al. |
| 2020/0179584 A1* | 6/2020 | Wabel ............ G01G 21/22 |

FOREIGN PATENT DOCUMENTS

| | | |
|---|---|---|
| WO | WO 2009148987 A2 | 12/2009 |
| WO | 2013067359 | 5/2013 |

* cited by examiner

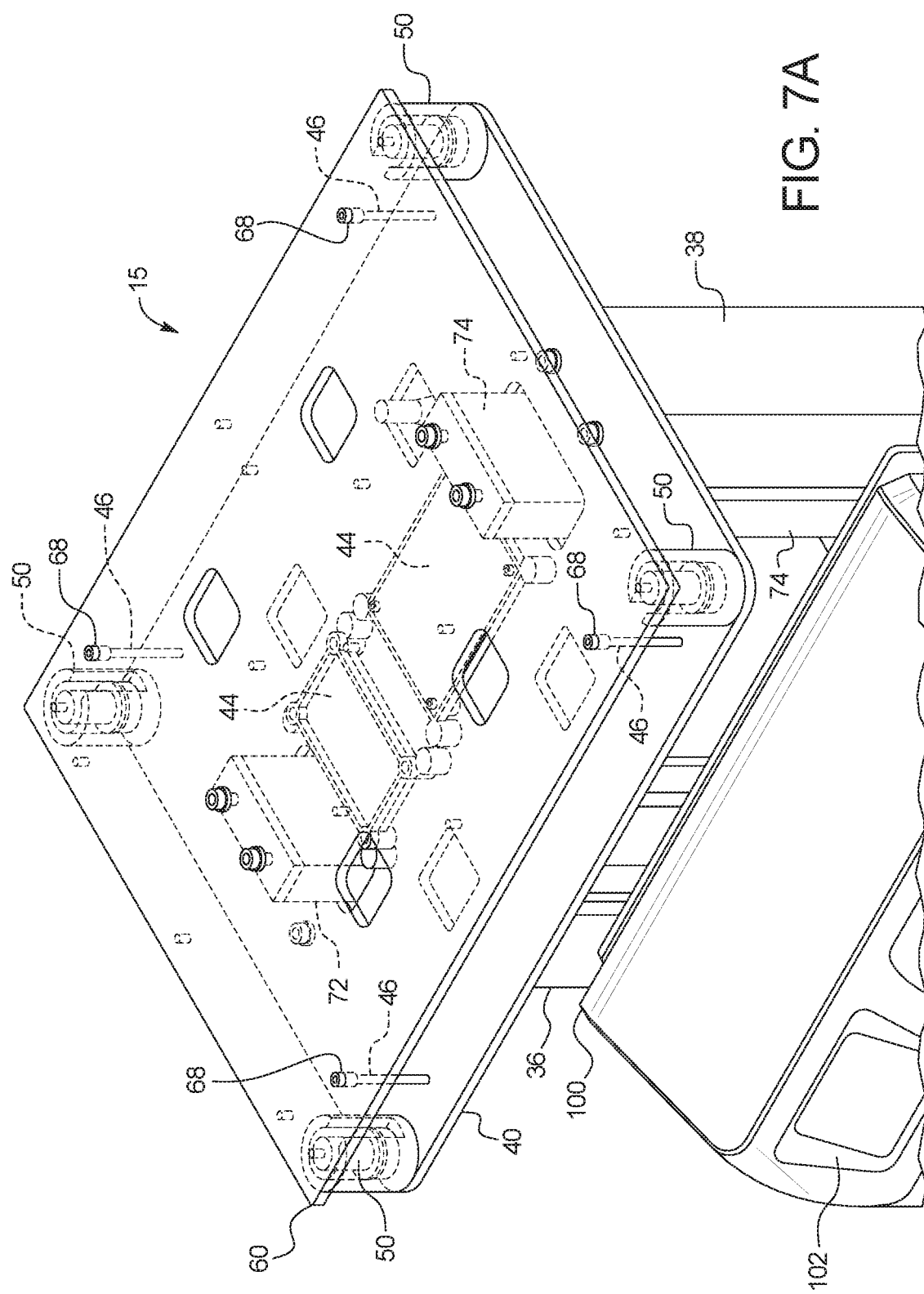

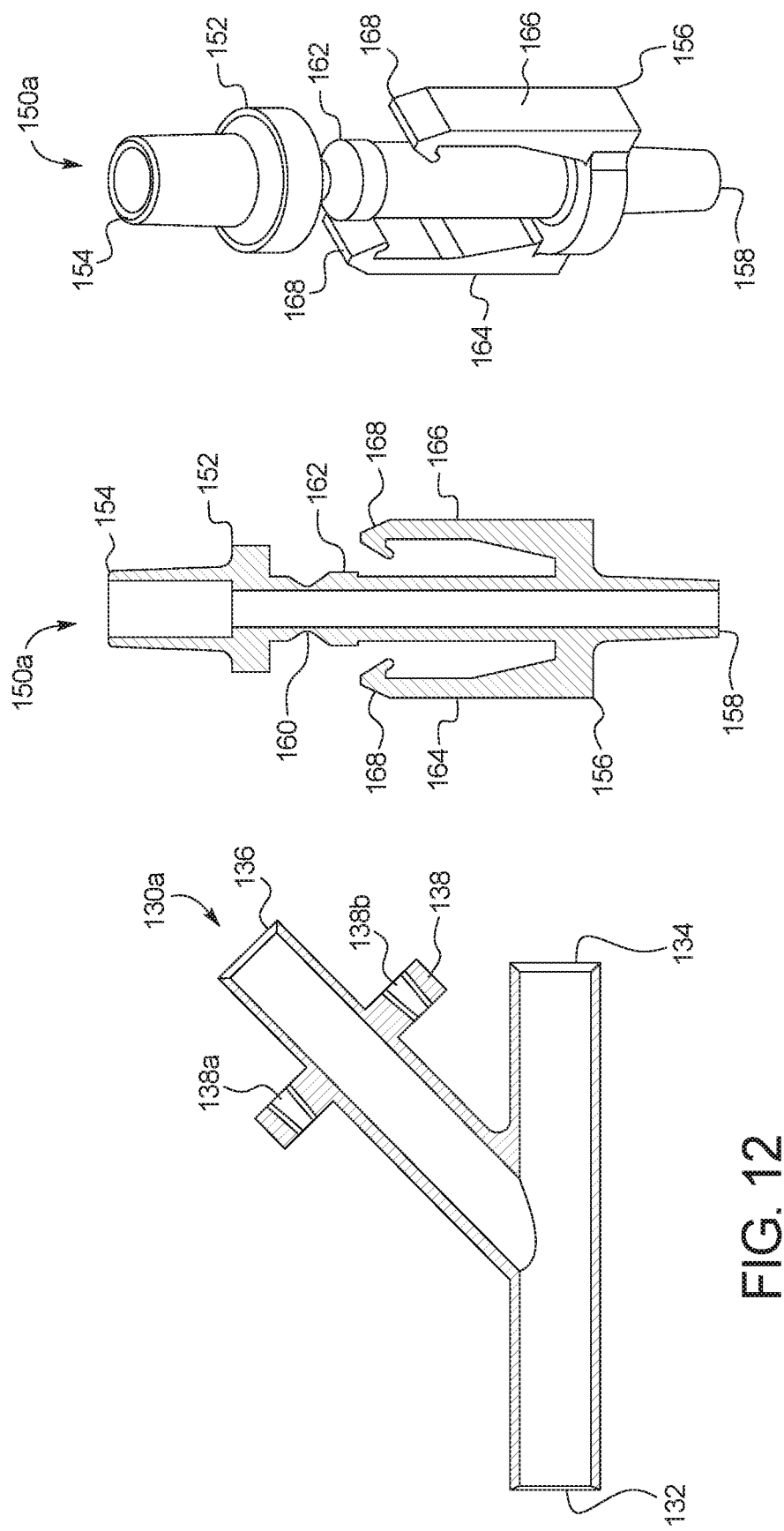

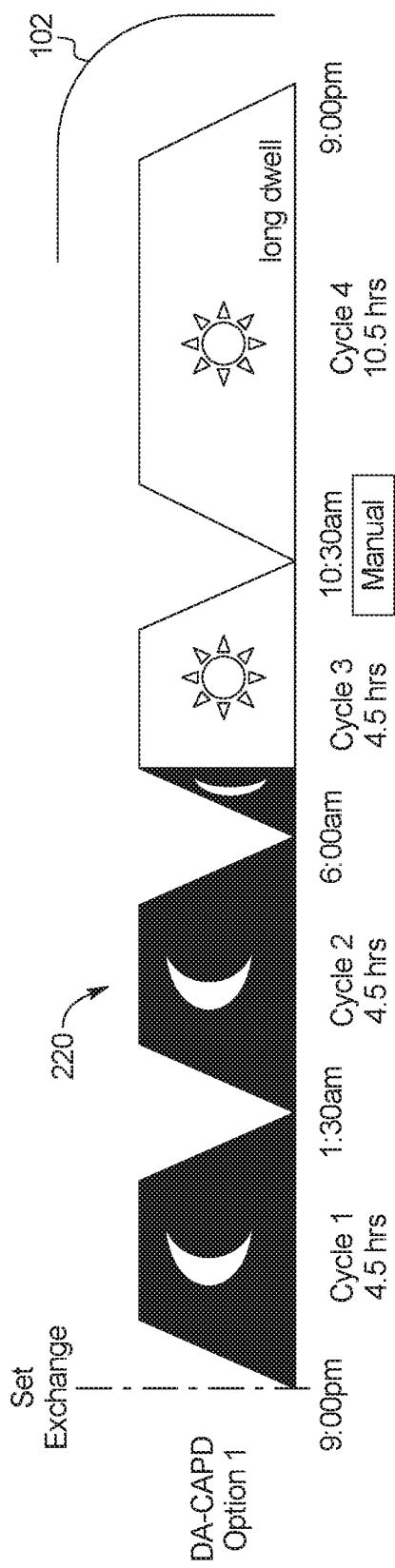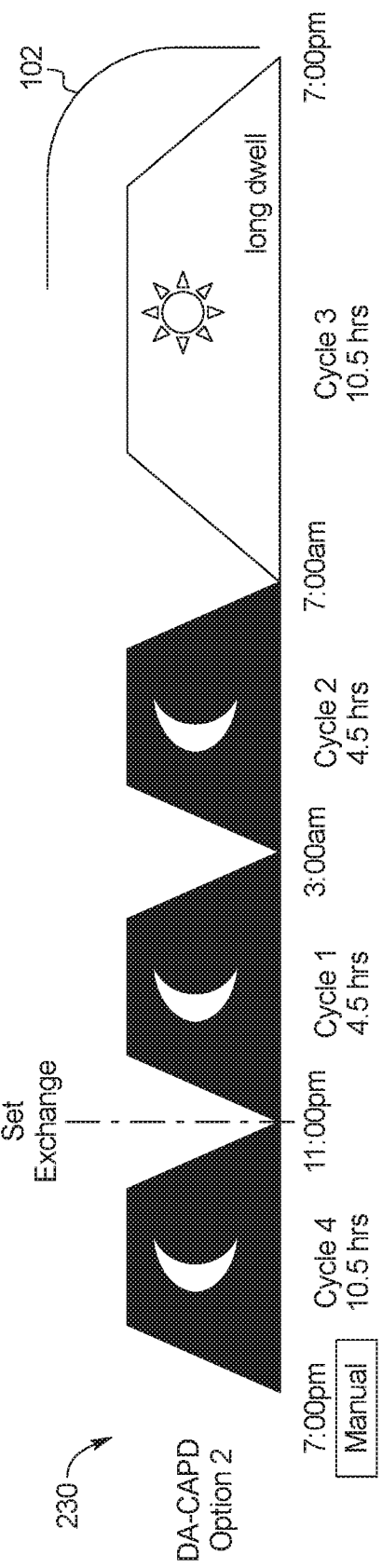

GRAVITY FED DIALYSIS SYSTEMS AND METHODS

PRIORITY

The present application is a divisional of U.S. application Ser. No. 15/946,395 filed Apr. 5, 2018, now U.S. Pat. No. 10,814,057, entitled "DISPOSABLE SET FOR A GRAVITY FED DIALYSIS SYSTEM".

BACKGROUND

The present disclosure relates generally to peritoneal dialysis and more specifically to gravity fed peritoneal dialysis.

Due to various causes, a person's renal system can fail. Renal failure produces several physiological derangements. The balance of water, minerals and the excretion of daily metabolic load is no longer possible and toxic end products of metabolism (e.g., urea, creatinine, uric acid, and others) can accumulate in blood and tissue.

Kidney failure and reduced kidney function have been treated with dialysis. Dialysis removes waste, toxins and excess water from the body that would otherwise have been removed by normal functioning kidneys. Dialysis treatment for the replacement of kidney function is critical to many people because the treatment is life saving.

Hemodialysis ("HD") and peritoneal dialysis ("PD") are two types of dialysis therapies used commonly to treat loss of kidney function. HD removes waste toxins and excess water from the patient's blood. The patient is connected to a hemodialysis machine via catheters inserted into a patient's vascular system. Blood is pumped from the patient, through the insides of hollow, porous tubes of a dialyzer connected to the machine, and back to the patient. The HD machine produces HD dialysis fluid, which is pumped outside of the hollow, porous tubes to cleanse the blood via osmosis. Excess blood water called ultrafiltration is pulled from the blood, through the pores of the membrane, into the dialysis fluid, where it is carried to a drain. Cleansed blood is returned to the patient. A large amount of dialysis fluid, for example about 120 liters, may be consumed to dialyze the blood during a single hemodialysis therapy. HD treatments may last several hours and may be performed in a treatment center approximately three or four times per week.

PD uses a PD dialysis fluid, which is infused into a patient's peritoneal cavity via a catheter. The PD dialysis fluid contacts the peritoneal membrane of the peritoneal cavity. Waste, toxins and excess water pass from the patient's bloodstream, through the peritoneal membrane, and into the dialysis fluid via osmosis, i.e., an osmotic gradient occurs across the membrane. Used dialysis fluid is drained from the patient, removing waste, toxins and excess water from the patient. The above cycle may be repeated.

There are various types of PD therapies, including continuous ambulatory peritoneal dialysis ("CAPD"), automated peritoneal dialysis ("APD"). CAPD is a manual dialysis treatment. The patient manually connects an implanted catheter to a drain, allowing used dialysis fluid, which had been previously infused into the patient in an earlier exchange, to drain from the patient's peritoneal cavity. The patient then connects the catheter to a bag of fresh dialysis fluid to infuse fresh dialysis fluid through the catheter and into the patient. The patient disconnects the catheter from the fresh dialysis bag and allows the dialysis fluid to dwell within the patient's peritoneal cavity, wherein the transfer of waste, toxins and excess water takes place as described herein. After the dwell period, the patient repeats the manual dialysis procedure, for example, four times per day, each of the procedures lasting about an hour.

CAPD is relatively inexpensive and is gravity driven, which is generally incapable of overpressurizing the patient. Patient data published in literature by Brandes et al. shows that flow rates during fill cycles are relatively constant and related to the patient's position (e.g., supine or sitting position) and the head height of the supply bag. Drain cycles however normally take about twice as long as fill cycles and have an antilog relationship with time. Within the gravity fed drain cycle, about 80% of intra-peritoneum volume is drained within the first 40% of the total drain time. Similar results are found from patient data by published in literature by Amici et al. Flow rates of gravity fill and drain may also be affected by several additional parameters, such as catheter type and tubing set type. CAPD also requires a significant amount of time and effort from the patient.

One known CAPD system provided by the assignee of the present disclosure includes two 2.5 liter solution bags, one empty and one full of fresh fluid. Tubes and clamps needed for treatment are provided with the two bags. The fresh bag is positioned above the patient, while empty drain bag is positioned below the patient. A line provided with the fresh fluid bag is unclamped, allowing fresh fluid to gravity flow to the patient and the fresh bag to empty. After a dwell period, a line provided with the empty drain bag is unclamped, allowing used dialysis fluid to gravity flow from the patient to the drain bag, filling the drain bag. The system is then discarded. To determine the amount of UF removed, the patient weighs the fresh fill bag prior to patient delivery and subtracts that weight from the weight of the full drain bag, taken after the drain is completed. The patient must then manually record the UF weight differential. If the patient is prescribed to perform multiple fill, dwell and drain cycles, as is typical, the above process is repeated using a new CAPD twin bag set. To determine the overall UF, e.g., over the course of twenty-four hours, the UF weight amounts from each of the individual CAPD sets are added.

APD is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to sources or bags of fresh dialysis solution, and to a fluid drain. APD machines pump fresh dialysis solution from the sources or bags, through the catheter, into the patient's peritoneal cavity, and allow the dialysis fluid to dwell within the patient's peritoneal cavity, causing the transfer of waste, toxins and excess water to take place. The APD machines then pump used dialysis fluid from the patient's peritoneal cavity to drain. As with the manual process, several drain, fill and dwell cycles occur during APD. A "last fill" may also occur at the end of both CAPD and APD, which remains in the peritoneal cavity of the patient until the next treatment or intermediate dialysis fluid exchange.

One downside of APD is cost. In certain areas of the world, APD machines are prohibitively expensive for the vast majority of patients. A need accordingly exists for a low cost way of providing a peritoneal dialysis treatment that may be performed while the patient sleeps, which eliminates or reduces the time and effort required of the patient undergoing CAPD, while still presenting a low cost per treatment.

SUMMARY

The examples described herein disclose a peritoneal dialysis ("PD") system that employs a gravity fed PD machine operating with a disposable set that is configured to reuse certain components to reduce disposable waste and cost. The gravity fed PD machine includes a frame that sits on castors and includes handles so that the machine may be moved readily from room to room within the patient's home or dwelling. The frame extends upwardly from the castors to a top plate mounted at the top of the frame. One or more load cell is mounted to the top plate. For example, a load cell may be mounted at each corner of the top plate. The load cells may each be provided with a load cell cup that mounts to the top plate, a load cell sensor located within the load cell cup, a compressible overload bushing that sits above the load cell sensor within the load cell cup, and a load applicator located between the load cell sensor and the compressible overload bushing.

A scale platform is placed on top of the load cells (e.g., on top of the compressible overload bushings) so as to be supported by, but not connected to, the load cells. In this manner, the one or more load cell sees and senses the entire weight placed onto and hanging from the scale platform. In one embodiment the weight placed onto the scale platform includes a supply container receiving tray sized to receive one or more fresh PD fluid supply container. In one implementation, the receiving tray sized to receive two, five liter fresh PD fluid bags.

In one embodiment the weight hanging from the scale platform includes a drain container support having plural, e.g., first and second, members mounted to and extending down from the scale platform. A drain container receiving portion of the drain container support is provided (e.g., attached) at the bottom of the first and second members extending down from the scale platform. A drain container receiving platform may be attached hingedly to the drain container receiving portion. A drain container receiving tray may then be removably set on the drain container receiving platform. One or more used PD fluid drain container may then be placed removably into the drain container receiving tray. The one or more used PD fluid drain container may be tilted as desired via the hinged relationship between drain container receiving platform and the drain container receiving portion.

The arrangement of the gravity fed machine may accordingly locate the fresh PD fluid supply containers at the top of the machine and the used PD fluid drain containers at or near the bottom of the machine, wherein a patient sitting or sleeping for treatment is located in an approximate middle of the machine, between the supply and drain containers. In this manner, fresh PD fluid may gravity flow from the fresh PD fluid supply containers to the patient, while used PD fluid may gravity flow from the patient to the used PD fluid drain containers. In an embodiment, the machine primes the disposable set initially with fresh PD fluid from the fresh PD fluid supply containers through to the drain valve prior to connecting the disposable set to the patient, so that if the patient is located below the drain valve during treatment, the used PD fluid may be siphoned from the patient, up past the drain valve, and down through the drain lines to the used PD fluid drain containers.

As described above, the scale platform in one embodiment supports both fresh and used PD fluids, such that the one or more load cell senses the weight of both the fresh and used PD fluids. The signals from the one or more load cells are sent to a control unit having one or more processor, one or more memory, a user interface (display device and input devices, e.g., touch screen and/or membrane switches), one or more data port (e.g., to accept a data card), electronics (e.g., for dual input voltage control), and in one embodiment a network connection (e.g., Ethernet). The control unit controls valves operating with the disposable set (e.g., a fresh PD fluid (to-patient) valve and a used PD fluid (from-patient) valve). The control unit may further control a heater (e.g., one or more resisitive heating coils) using feedback to the control unit via one or more temperature sensor, wherein the heater and temperature sensors are located below the supply container receiving tray to heat the tray and the fresh PD fluid containers placed upon the tray, so that the fresh PD fluid is heated to a desired temperature, e.g., body temperature or 37° C.

Regarding PD fluid control, the control unit knows from the load cells how much fresh PD fluid is loaded initially onto the supply container receiving tray, e.g., the weight of two, five liter bags of fresh PD fluid. After a first patient fill, the control unit knows from the load cells how much fresh PD fluid has been delivered to the patient, e.g., by how much the weight drops. After a first patient dwell and drain, wherein used dialysis fluid is removed to a used PD fluid drain container, the control unit knows from the load cells how much used PD fluid and additional ultrafiltration ("UF") has been removed from the patient, e.g., by how much the weight increases, now with fluid residing in both fresh (located above the scale platform) and used (located below the scale platform) PD fluid containers. After the first patient fill, dwell and drain, and assuming a complete drain, it is expected that the control unit sees more weight than the initial fresh PD fluid weight due to UF removal from the patient. Second, third, fourth, etc., fill, dwell and drain cycles operate in a same manner as described above, in which fill amounts are determined by a weight drop due to fresh PD fluid gravity flowing from the machine to the patient, while drain amounts are determined by a weight increase due to used PD fluid and UF gravity flowing from the patient to the machine.

When all fresh PD fluid has been drained from the fresh PD fluid supply containers and all used PD fluid and UF have been drained from the patient to the used PD fluid drain containers, the control unit may calculate a total amount of UF removed from the patient for the treatment by subtracting the initial total fresh fluid amount from the final total used fluid amount. In the above manner, per cycle and total UF amounts may be determined by the control unit and load cell arrangement of the present disclosure. Such amounts may be displayed to the user in the dialysis device of the user interface and recorded for downloading to an external memory device, e.g., universal serial bus ("USB") flash drive, or in one embodiment for uploading to a network and/or remote server via a network connection.

In one embodiment, the disposable set of the present disclosure reuses the supply line and the connected fresh PD fluid supply containers from a previous treatment in a current treatment. The disposable set includes a multi-port connector, e.g., a three-way connector, such as a Y-connector or T-connector. A patient line attaches at one end to a first port of the multi-port connector and at the other end to a patient. A supply line attaches at one end to a second port of the multi-port connector and at the other end to one or more fresh PD fluid supply container (e.g., forks or splits into two or more branch lines leading to multiple supply containers). A drain line attaches at one end to a third port of the multi-port connector and at the other end to one or more used PD fluid drain container (e.g., forks or splits into two or more branch lines leading to multiple drain containers). The drain line and drain containers in an embodiment served as the supply line and supply containers in a previous treatment, which is made possible because (i) the supply containers are empty at the end of a treatment, (ii) the supply line does not at least in any significant amount touch effluent fluid from the patient, and (iii) the reused line and base are used in a subsequent treatment for the same patient.

In various embodiments, the connector of the supply line that connects to the second port of the multi-port connector includes a frangible portion that the user breaks so that a portion of the connector remains and is discarded with the multi-port connector, the patient line and the drain line. A remainder of the connector is resued and includes a secondary connection portion that removably seals to the third port of the new multi-port connector. The removable seal is configured to provide a suitable fluid-tight connection while still requiring a connection force that is not undue for the patient who may be elderly to supply. In the same manner, the frangible portion is configured such that its breaking force is not undue.

The gravity flow PD system of the present disclosure is configured to provide different types of automated PD treatments in one embodiment. The treatments may be programmed into the control unit at the machine, and may be downloaded to the control unit over a network, and/or uploaded to the control unit from a remote data storage device, e.g., USB drive. The control unit may for example provide the patient with a choice to perform either an automated peritoneal dialysis ("APD") treatment or a device-assisted continuous ambulatory peritoneal dialysis ("DA-CAPD") treatment. The primary differences between APD treatments and DA-CAPD treatments are that (i) there are more automated cycles in APD treatments versus DA-CAPD and because of that (ii) fill volumes for APD treatments are typically different (e.g., less) than for DA-CAPD treatments, and (iii) dwell times for APD treatments are typically different (e.g., less) than for DA-CAPD treatments. DA-CAPD treatments also likely have more manual exchange steps than APD treatments.

The control unit may allow the patient to run an APD treatment one day and a DA-CAPD treatment the next day and vice versa. The control unit may also store multiple APD treatments and multiple DA-CAPD treatments and allow the patient to pick a desired treatment to be run for one or more consecutive days.

In light of the disclosure herein and without limiting the disclosure in any way, in a first aspect of the present disclosure, which may be combined with any other aspect listed herein unless specified otherwise, a gravity fed peritoneal dialysis ("PD") machine includes: a frame configured to be set on a supporting surface; at least one load cell; a scale platform supported by the frame via the at least one load cell positioned between the frame and the scale platform; and a drain container support in mechanical communication with and extending downwardly from the scale platform when the frame is set on the supporting surface, wherein the machine is configured such that when the frame is set on the supporting surface, at least one fresh PD fluid supply container is supportable by the scale platform above the at least one load cell and at least one used PD fluid drain container is supportable by the drain container support below the at least one load cell, so that a combined weight of fresh PD fluid and used PD fluid may be sensed by the at least one load cell.

In a second aspect of the present disclosure, which may be combined with any other aspect listed herein unless specified otherwise, the drain container support includes plural members in mechanical communication with and extending downwardly from the scale platform, and a drain container receiving portion located between the plural members.

In a third aspect of the present disclosure, which may be combined with the second aspect in combination with any other aspect listed herein unless specified otherwise, the dialysis machine includes a drain container receiving tray removably placeable above the drain container receiving portion of the drain container support, the drain container receiving tray sized to accept the at least one used PD fluid drain container.

In a fourth aspect of the present disclosure, which may be combined with the second aspect in combination with any other aspect listed herein unless specified otherwise, the frame includes plural legs each defining a contour, and wherein the plural members of the drain container support each define a contour matching the contour of at least one of the legs.

In a fifth aspect of the present disclosure, which may be combined with any other aspect listed herein unless specified otherwise, the drain container support is connected directly to the scale platform.

In a sixth aspect of the present disclosure, which may be combined with any other aspect listed herein unless specified otherwise, the scale platform includes plural corners, and which includes plural load cells, including one load cell supporting each corner of the scale platform, between the scale platform and the frame.

In a seventh aspect of the present disclosure, which may be combined with any other aspect listed herein unless specified otherwise, the dialysis machine includes a supply container receiving tray in mechanical communication with the scale platform, the supply container receiving tray sized to accept the at least one fresh PD fluid supply container.

In an eighth aspect of the present disclosure, which may be combined with the seventh aspect in combination with any other aspect listed herein unless specified otherwise, at least one of the scale platform or the supply container receiving tray is configured to support the at least one fresh PD fluid supply container at an angle that directs the fresh PD fluid towards a lowered outlet portion of the supply container.

In a ninth aspect of the present disclosure, which may be combined with the seventh aspect in combination with any other aspect listed herein unless specified otherwise, the dialysis machine includes a heater positioned and arranged to heat the supply container receiving tray to in turn the at least one fresh PD fluid supply container.

In a tenth aspect of the present disclosure, which may be combined with any other aspect listed herein unless specified otherwise, the dialysis machine includes a control unit, a first valve under control of the control unit to selectively allow fresh PD fluid to gravity flow from the at least one fresh PD fluid supply container to a patient, and a second valve under control of the control unit to selectively allow used PD fluid to gravity flow from the patient to the at least one used PD fluid drain container.

In an eleventh aspect of the present disclosure, which may be combined with the tenth aspect in combination with any other aspect listed herein unless specified otherwise, the at least one load cell is in signal communication with the control unit.

In a twelfth aspect of the present disclosure, which may be combined with the tenth aspect in combination with any other aspect listed herein unless specified otherwise, the control unit includes a user interface, the user interface including a display and at least one input device, the control unit programmed to display a plurality of different PD treatment types and to enable a user to select one of the treatment types for an upcoming treatment using the at least one input device.

In a thirteenth aspect of the present disclosure, which may be combined with the twelfth aspect in combination with any other aspect listed herein unless specified otherwise, a first one of the PD treatment types includes automated peritoneal dialysis and a second one of the PD treatment types includes device-assisted continuous ambulatory peritoneal dialysis.

In a fourteenth aspect of the present disclosure, which may be combined with any other aspect listed herein unless specified otherwise, the at least one load cell includes a load cell mounting cup supporting a load cell sensor, the load cell mounting cup mounted to the frame and housing a load applicator positioned and arranged to deliver a load to the load cell sensor, the load applicator in mechanical communication with the scale platform.

In a fifteenth aspect of the present disclosure, which may be combined with any other aspect listed herein unless specified otherwise, a gravity fed peritoneal dialysis ("PD") machine includes: a frame configured to be set on a supporting surface; at least one load cell; a scale platform supported by the frame via the at least one load cell positioned between the frame and the scale platform; a drain container support in mechanical communication with and extending downwardly from the scale platform when the frame is set on the supporting surface, wherein the machine is configured such that when the frame is set on the supporting surface, at least one fresh PD fluid supply container is supportable by the scale platform above the at least one load cell and at least one used PD fluid drain container is supportable by the drain container support below the at least one load cell; and a control unit configured to monitor an instantaneous combined weight of fresh PD fluid and used PD fluid via feedback from the at least one load cell, wherein the control unit is configured to determine an amount of a patient fill of fresh PD fluid by recording a decrease in the instantaneous combined weight, and the control unit is configured to determine an amount of a patient drain of used PD fluid by recoding an increase in the instantaneous combined weight.

In a sixteenth aspect of the present disclosure, which may be combined with the fifteenth aspect in combination with any other aspect listed herein unless specified otherwise, the control unit is further configured to determine an amount of ultrafiltration removed from a patient by differentiating the amount of the patient fill from the amount of the patient drain.

In a seventeenth aspect of the present disclosure, which may be combined with the sixteenth aspect in combination with any other aspect listed herein unless specified otherwise, the differentiating occurs (i) after multiple patient drains and summing the resulting amounts of the ultrafiltration removed or (ii) once after summing multiple patient fill amounts and patient drain amounts.

In an eighteenth aspect of the present disclosure, which may be combined with any other aspect listed herein unless specified otherwise, a peritoneal dialysis ("PD") system includes: a disposable set including at least one fresh PD fluid supply container, at least one used PD fluid drain container and tubing located between the at least one fresh PD fluid supply container and the at least one used PD fluid drain container; and a gravity fed PD machine operable with the disposable set, the gravity fed PD machine including a frame configured to be set on a supporting surface, at least one load cell, a scale platform supported by the frame via the at least one load cell positioned between the frame and the scale platform, and a drain container support in mechanical communication with and extending downwardly from the scale platform when the frame is set on the supporting surface, wherein the machine is configured such that when the frame is set on the supporting surface, the at least one fresh PD fluid supply container is supportable by the scale platform above the at least one load cell and the at least one used PD fluid drain container is supportable by the drain container support below the at least one load cell, so that a combined weight of fresh PD fluid and used PD fluid may be sensed by the at least one load cell.

In a nineteenth aspect of the present disclosure, which may be combined with the eighteenth aspect in combination with any other aspect listed herein unless specified otherwise, the gravity fed PD machine includes at least one valve configured to operate with the tubing located between at least one fresh PD fluid supply container and the patient, and at least one valve configured to operate between the patient and at least one used PD fluid drain container.

In a twentieth aspect of the present disclosure, which may be combined with any other aspect listed herein unless specified otherwise, a peritoneal dialysis ("PD") system includes: a disposable set including at least one fresh PD fluid supply container, at least one used PD fluid drain container and tubing located between the at least one fresh PD fluid supply container and the at least one used PD fluid drain container; and a gravity fed PD machine operable with the disposable set, the gravity fed PD machine including a control unit having a user interface and at least one input device, wherein the control unit is configured to provide an option to a user to perform either (i) an automated peritoneal dialysis ("APD") treatment in which three or more patient fills are performed using one or more APD dwell duration, or (ii) a device-assisted continuous ambulatory peritoneal dialysis (DA-CAPD) treatment in which two patient fills are performed using one or more DA-CAPD dwell duration, wherein an average DA-CAPD dwell duration is longer than an average APD dwell duration.

In a twenty-first aspect of the present disclosure, which may be combined with the twentieth aspect in combination with any other aspect listed herein unless specified otherwise, a DA-CAPD treatment patient fill uses a variable, e.g., greater, amount of fresh PD fluid than does an APD patient fill.

In a twenty-second aspect of the present disclosure, which may be combined with the twentieth aspect in combination with any other aspect listed herein unless specified otherwise, the DA-CAPD treatment includes more manual steps than does the APD treatment.

In a twenty-third aspect of the present disclosure, which may be combined with any other aspect listed herein unless specified otherwise, a disposable set for a dialysis treatment includes: a patient line including a first connector configured to connect to a patient connector and a second connector configured to connect to a first port of a multi-port connector; and a supply line including a first connector configured to connect to a PD fluid supply container and a second connector configured to connect to a second port of the multi-port connector, wherein the second connector of the supply line includes a frangible portion allowing, after the dialysis treatment, the supply line and a secondary connection portion of the second connector remaining after the frangible portion is broken to be used as a drain line for a subsequent dialysis treatment, wherein a third port of the multi-port connector is configured to allow a supply line and secondary connection portion from a prior dialysis treatment to be used as a drain line for the dialysis treatment, and wherein the secondary connection portion from the prior dialysis treatment is configured to removably seal to the third port for the dialysis treatment.

In a twenty-fourth aspect of the present disclosure, which may be combined with the twenty-third aspect in combination with any other aspect listed herein unless specified otherwise, the multi-port connector includes a Y-connector or a T-connector.

In a twenty-fifth aspect of the present disclosure, which may be combined with the twenty-third aspect in combination with any other aspect listed herein unless specified otherwise, the disposable set further includes the PD fluid supply container connected to the first connector, the PD fluid supply container used as a PD fluid drain container for the subsequent treatment.

In a twenty-sixth aspect of the present disclosure, which may be combined with the twenty-fifth aspect in combination with any other aspect listed herein unless specified otherwise, the PD fluid supply container is oversized relative to an amount of fresh PD fluid stored in the PD fluid supply container to be able to store an amount of ultrafiltration removed from a patient when operating as the PD fluid drain container.

In a twenty-seventh aspect of the present disclosure, which may be combined with the twenty-third aspect in combination with any other aspect listed herein unless specified otherwise, the first connector of the supply line is a first, first connector, and wherein the supply line splits into a first branch and a second branch, the first branch leading to the first, first connector connectable to a first PD fluid supply container, and the second branch leading to a second, first connector connectable to a second PD fluid supply container.

In a twenty-eighth aspect of the present disclosure, which may be combined with the twenty-seventh aspect in combination with any other aspect listed herein unless specified otherwise, the first PD fluid supply container is used as a first PD fluid drain container for the subsequent treatment, and the second PD fluid supply container is used as a second PD fluid drain container for the subsequent treatment.

In a twenty-ninth aspect of the present disclosure, which may be combined with the twenty-seventh aspect in combination with any other aspect listed herein unless specified otherwise, the supply line includes a common section between the second connector of the supply line and the first and second branches, and which includes a line clamp fitted to the common section, the line clamp closed prior to breaking the frangible portion of the second connector of the supply line.

In a thirtieth aspect of the present disclosure, which may be combined with the twenty-third aspect in combination with any other aspect listed herein unless specified otherwise, the third port of the multi-port connector includes a flange, and wherein the secondary connection portion includes at least one hook sized and arranged to removably (e.g., snap-fittingly) hook to the flange of the third port when the secondary connection portion is removably sealed to the third port.

In a thirty-first aspect of the present disclosure, which may be combined with the twenty-third aspect in combination with any other aspect listed herein unless specified otherwise, the secondary connection portion includes an outer diameter larger than an inner diameter of the third port of the multi-port connector for removably (e.g., press-fittingly) sealing the secondary connection portion to the third port.

In a thirty-second aspect of the present disclosure, which may be combined with any other aspect listed herein unless specified otherwise, a disposable set for a dialysis treatment includes: a patient line including a first connector configured to connect to a patient connector and a second connector configured to connect to a first port of a multi-port connector; and a supply line including a first connector configured to connect to a PD fluid supply container and a second connector configured to connect to a second port of the multi-port connector, wherein the supply line is configured to allow, after the dialysis treatment, at least a portion of the second connector and the tubing of the supply line to be used as a drain line for a subsequent dialysis treatment, wherein a third port of the multi-port connector is configured to allow tubing and at least a portion of a second connector of a supply line from a prior dialysis treatment to be used as a drain line for the dialysis treatment, and wherein the at least a portion of the second connector from the prior dialysis treatment is configured to removably seal to the third port.

In a thirty-third aspect of the present disclosure, which may be combined with the thirty-second aspect in combination with any other aspect listed herein unless specified otherwise, the second connector includes a frangible portion enabling the at least a portion of the second connector and the tubing of the supply line to be broken off at the frangible portion and used as the drain line for the subsequent dialysis treatment.

In a thirty-fourth aspect of the present disclosure, any of the structure and functionality disclosed in connection with FIGS. 1 to 19 may be combined with any of the other structure and functionality disclosed in connection with FIGS. 1 to 19.

In light of the present disclosure and the above aspects, it is therefore an advantage of the present disclosure to provide an improved gravity fed PD machine.

It is another advantage of the present disclosure to provide an improved PD disposable.

It is a further advantage of the present disclosure to reduce disposable waste and cost.

It is still another advantage of the present disclosure to lower the amount of manual continuous ambulatory PD actions and steps.

It is still a further advantage of the present disclosure to provide a gravity fed PD machine that is efficient and cost effective to build.

It is yet another advantage of the present disclosure to provide a gravity fed PD machine that controls fresh and used fluid delivery and UF removed amounts accurately.

The advantages discussed herein may be found in one, or some, and perhaps not all of the embodiments disclosed herein. Additional features and advantages are described herein, and will be apparent from, the following Detailed Description and the figures.

BRIEF DESCRIPTION OF THE FIGURES

FIG. 7A is a top, front perspective view of one embodiment for a load cell arrangement useable with the gravity fed dialysis machine of FIGS. 2 to 5.

FIG. 12 is a front elevation sectional view of one embodiment of a multi-port connector used with the disposable sets of the present disclosure.

FIG. 13A is a front sectioned view of one embodiment of a frangible connector used with the multi-port connector of FIG. 12.

FIG. 13B is a top, front perspective view of the frangible connector of FIG. 13A used with the multi-port connector of FIG. 12.

FIG. 18 illustrates a second example device-assisted continuous ambulatory peritoneal dialysis ("DA-CAPD") treatment displayed on a display device of and performable by the PD system of the present disclosure.

FIG. 19 illustrates a third example device-assisted continuous ambulatory peritoneal dialysis ("DA-CAPD") treatment displayed on a display device of and performable by the PD system of the present disclosure.

DETAILED DESCRIPTION

Gravity Fed Machine and System

Figure 1:
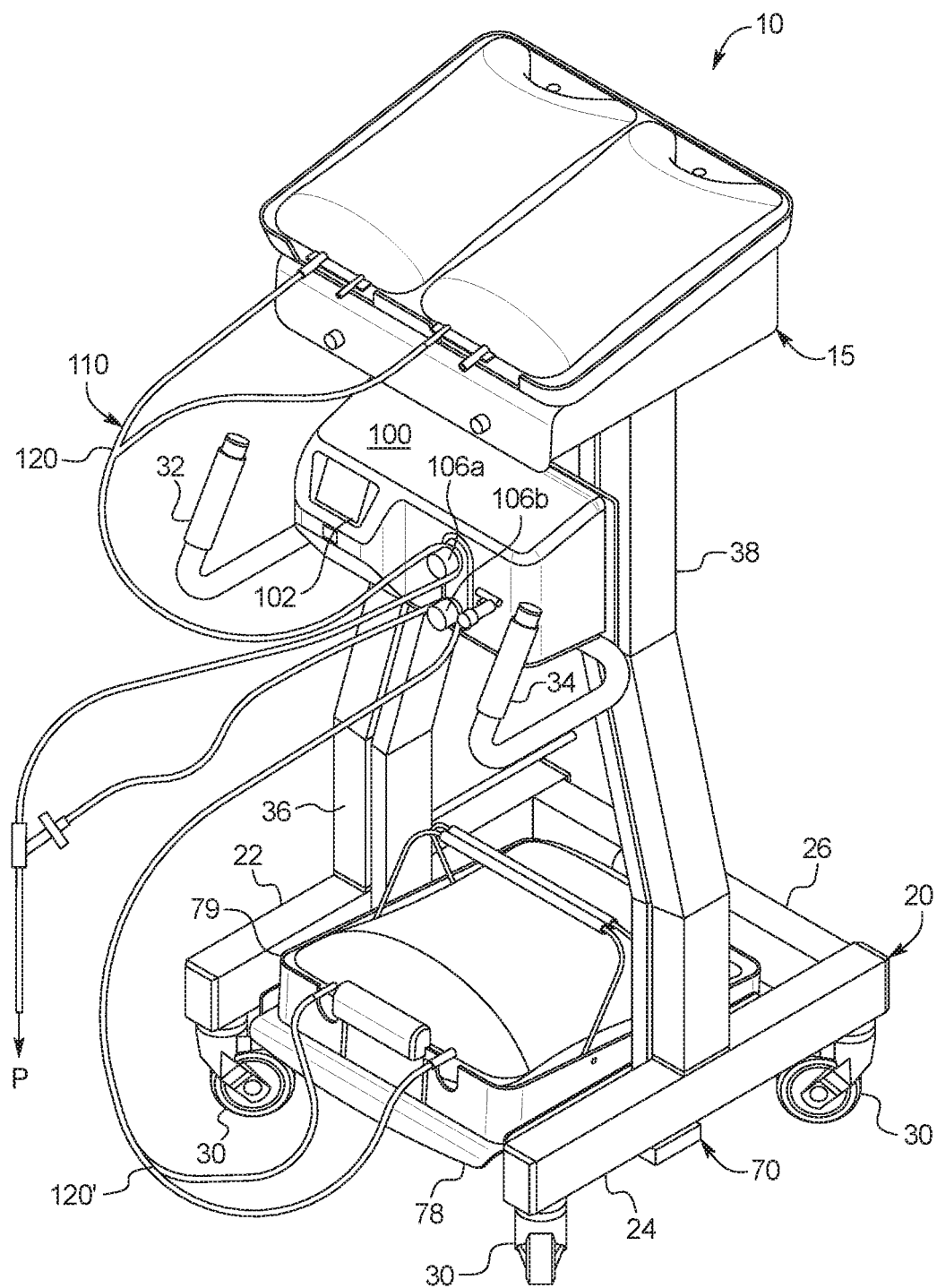
FIG. 1 is a top, front perspective view of one embodiment of a peritoneal dialysis system of the present disclosure.

Referring now to the drawings and in particular to FIG. 1, a peritoneal dialysis ("PD") system 10 is illustrated. PD system 10 includes a PD machine 15 and a disposable set 110. PD machine 15 is in one embodiment a gravity fed PD machine. In one embodiment, gravity fed machine 15 uses no pump and relies upon gravity for all fluid movement. In an alternative embodiment, gravity fed machine 15 may employ one or more pump, e.g., a pump for removing used PD fluid from the patient to a drain. Disposable set 110 is illustrated and discussed in detail below. FIGS. 2 to 5 provide different views of machine 15.

PD machine 15 in the illustrated embodiment includes a frame 20 made of a suitably strong material, such as stainless steel, steel, aluminum, fiberglass or a plastic, such as polyethyene or polypropylene. Frame 20 in the illustrated embodiment includes a base made up of three members 22, 24 and 26 that are bolted, welded, adhered or formed integrally together. In the illustrated embodiment, the base of frame 20 does not include a front member so that at least one used PD fluid drain container of disposable set 110 may be easily lifted into and removed from the base. It should be appreciated that the base of frame 20 in the illustrated embodiment does not support the weight of the at least one used PD fluid drain container directly. The base of frame 20 is large enough however to extend around the at least one used PD fluid drain container.

Figure 5:
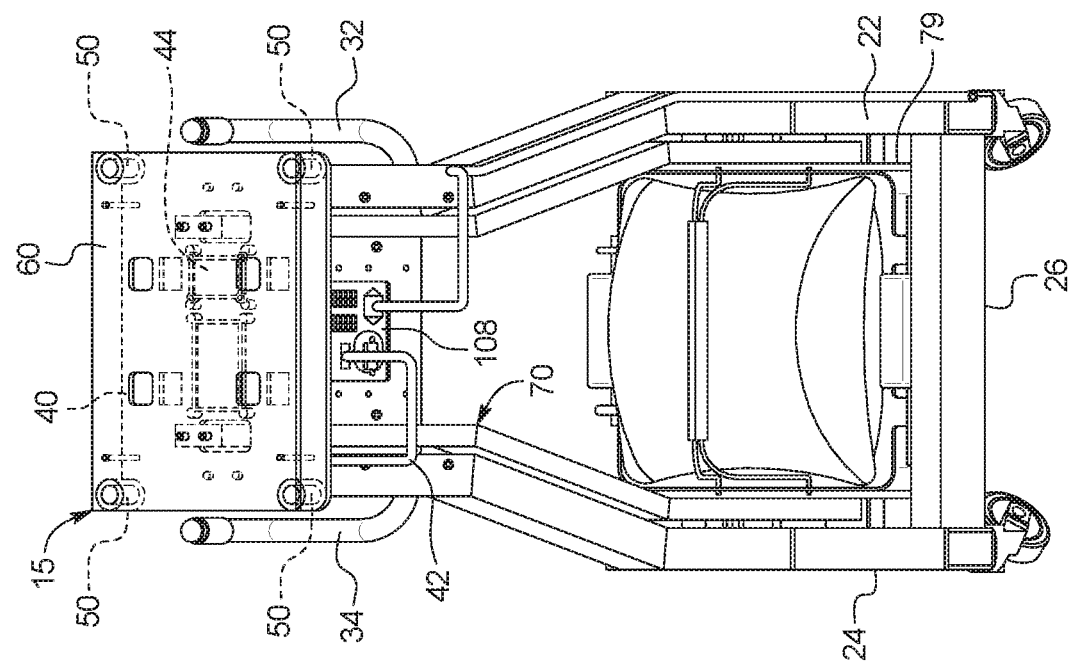
FIG. 5 is a rear elevation view of the gravity fed dialysis machine embodiment of FIG. 2.
Figure 6:
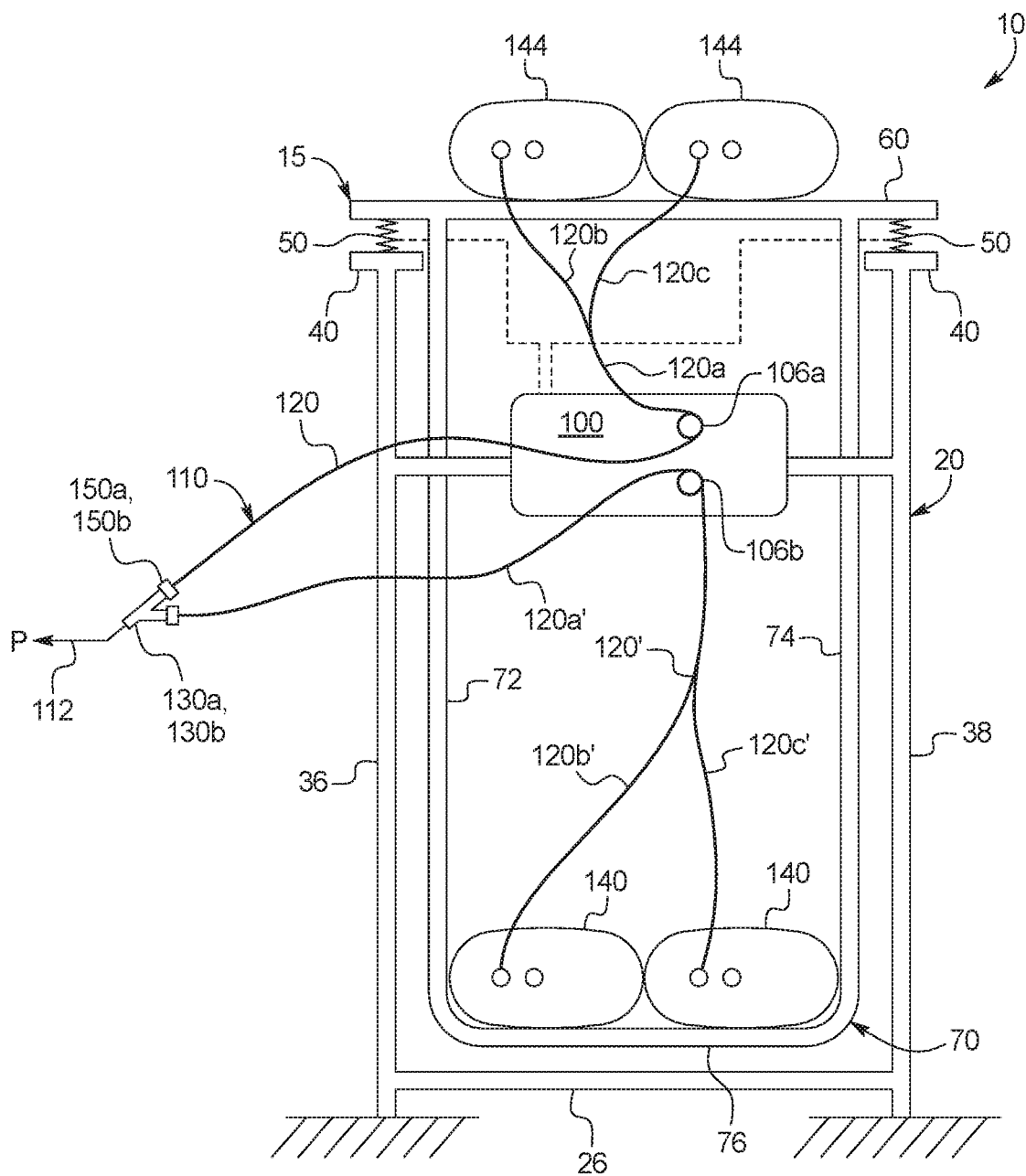
FIG. 6 is a schematic view illustrating one embodiment for a fresh and used dialysis solution weight suspension system and method of the present disclosure.

Plural castors 30 are connected to the bottoms of side members 22 and 24 of the base of frame 20, so that PD system 10 may be moved easily using handles 32 and 34 connected to frame 20. Legs 36 and 38 extend up from members 22 and 24, respectively, of the base of frame 20. Legs 36 and 38 may be bolted to, welded to, adhered to, or formed integrally with members 22 and 24, respectively. FIGS. 5 and 6 illustrate that legs 36 and 38 terminate at their upper ends at a top plate 40 in one embodiment. Legs 36 and 38 may be bolted to, welded to, adhered to, or formed integrally with top plate 40.

Top plate 40 may be considered to be the top of frame 20, wherein all structure located above top plate 40 is supported by load cells 50. In the illustrated embodiment of FIG. 7A for example, four load cells 50 are provided, one at each of the corners of top plate 40. Less or more load cells 50, including a single, central load cell may be provided on top plate 40 if desired. In an embodiment, load cells 50 are spaced apart from each other so as to evenly support a scale platform 60 resting on top of load cells 50. In the illustrated embodiment, four load cells 50 are provided, one at each of the corners of scale platform 60.

Figure 3:
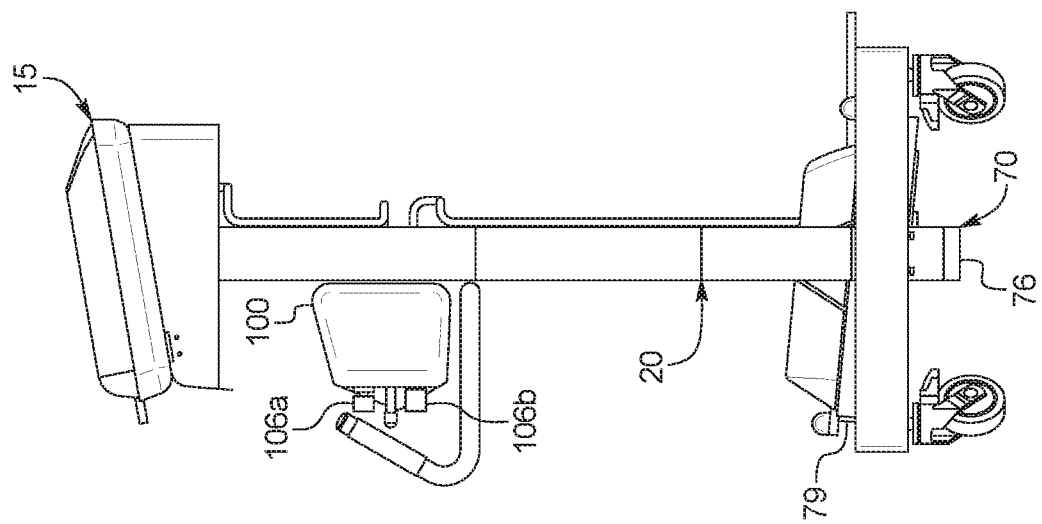
FIG. 3 is a side elevation view of the gravity fed dialysis machine embodiment of FIG. 2.
Figure 2:
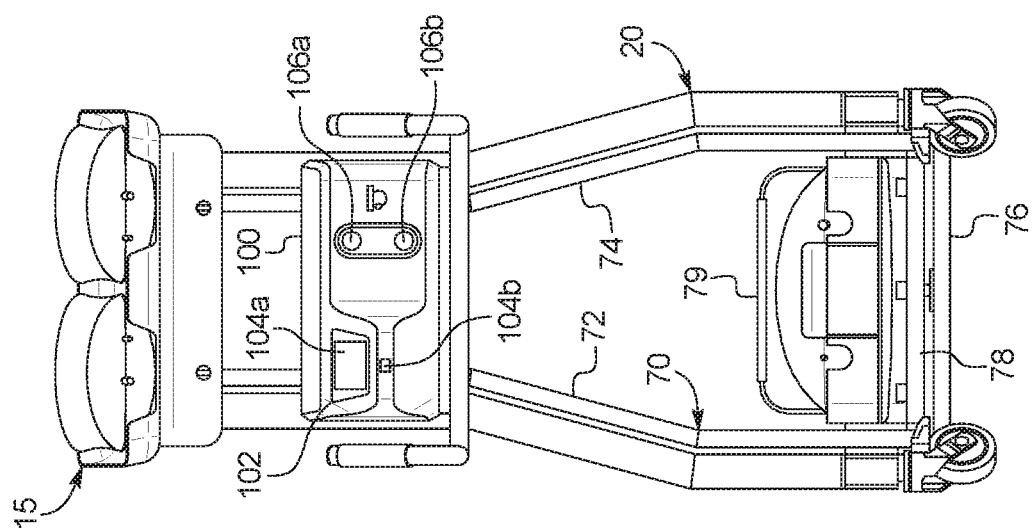
FIG. 2 is a front elevation view of one embodiment of a gravity fed dialysis machine for use with the system of FIG. 1.

FIGS. 1 to 5 illustrate that machine 15 further includes a drain container support 70. Drain container support 70 in the illustrated embodiment includes plural members 72 and 74 in mechanical communication with, e.g., connected to or formed integrally with, and extending downwardly from scale platform 60. Additionally, members 72 and 74 are in mechanical communication with, e.g., connected to, or are formed integrally with a drain container receiving portion 76 located between members 72 and 74. In the illustrated embodiment, a drain container receiving platform 78 is fixed to and sits above drain container receiving portion 76. As illustrated in FIGS. 2 and 3, drain container receiving platform 78 may be hingedly fixed to drain container receiving portion 76, so that one or more used PD fluid drain container located within a drain container receiving tray 79 may be tilted as desired for ready placement into and removal from machine 15.

It should be appreciated that legs 36 and 38 of frame 20 connected to top plate 40 provide rigidity to three member 22, 24 and 26 base of frame 20, tending to prevent members 22 and 24 from bending outward from each other or inward towards each other. Also, members 72 and 74 of drain container support 70 are sized and shaped to align with and follow the contour of legs 36 and 38 of frame 20. In this manner, scale platform 60 and drain container support 70, which float along (are not attached to) load cells 50, are constrained laterally between legs 36 and 38 of frame 20. This in combination with the weight placed upon load cells, the provision of pins and receiving apertures (discussed below), the construction of load cells 50 (discussed below), and side panels (discussed below) attached to scale platform 60 prevent platform 60 from being able to slide off of top plate 40.

FIGS. 1 to 5 illustrate that gravity fed PD machine 15 further includes a control unit 100 in one embodiment. Control unit 100 includes one or more microprocessor operating with one or more memory, which is (are) programmed to store one or more peritoneal dialysis treatment as discussed in detail below. Control unit 100 may further include a video controller operable with the one or more microprocessor operating with the one or more memory to control a user interface 102, including a display 104a and at least one input device 104b. Input device 104b may be one or more electromechanical button, such as a membrane switch, and/or a touch screen overlay operating with display 104a. Display 104a may be a liquid crystal display ("LCD") or a light emitting diode ("LED") display.

FIGS. 2 and 3 illustrate that control unit 100 is in one embodiment provided with plural valves, such as a fresh PD fluid (to-patient) valve 106a and a used PD fluid (from-patient) valve 106b. Valves 106a and 106b may be electrically actuated solenoid valves under control of control unit 160. In an embodiment, valves 106a and 106b are spring closed and energized open to provide fail safe operation upon power loss. In general, during a patient fill, control unit 100 will cause upper fresh PD fluid valve 106a to be energized open, while lower used PD fluid valve 106b is unenergized and closed. During a patient drain, control unit 100 will cause lower used PD fluid valve 106b to be energized open, while upper fresh PD fluid valve 106a is unenergized and closed. During a patient dwell, control unit 100 will cause both valves 106a and 106b to be unenergized and closed.

FIG. 6 illustrates schematically one embodiment for suspending fresh PD fluid supply containers 144 and used PD fluid drain containers 140 using system 10 and the associated methodology of the present disclosure. System 10 includes frame 20 having legs 36 and 38 mechanically linked via members 22, 24 and 26 (only member 26 viewable in FIG. 6) as has been described herein. Frame 20 sits on a supporting surface or ground as illustrated. Frame 20 also includes a top plate 40, which is illustrated in FIG. 6 as being separate pedastals or flanges located at the upper ends of legs 36 and 38. A drain container support 70 is located inside of frame 20 in the illustrated embodiment. Drain container support 70 includes side members 72 and 74 joined together via a drain container receiving portion 76 of support 70. Side members 72 and 74 of drain container support 70 are mechanically linked or attached at their upper ends to a scale platform 60.

Control unit 100 in FIG. 6 is supported by frame 20 in the illustrated embodiment. Control unit 100 includes control valves 106a and 106b as described herein. Disposable set 110 includes fresh PD fluid supply containers 144, used PD fluid drain containers 140 and tubing in between, which is described in detail below. The element numbers for the tubing and for other components of disposable set are provided in FIG. 6 to show one embodiment for their positioning during use with machine 15. Fresh fluid tubing 120a, 120b, 120c runs from fresh PD fluid supply containers 144, through fresh PD fluid (to-patient) valve 106a, to patient P. Used fluid tubing 120a, 120b, 120c runs from patient P, through used PD fluid (from-patient) valve 106b, to used PD fluid drain containers 140. Fresh PD fluid gravity flows from fresh PD fluid supply containers 144 to patient P and from patient P (e.g., via syphoning) to used PD fluid drain containers 140.

As illustrated in FIG. 6, scale platform 60, drain container support 70, fresh PD fluid supply containers 144, used PD fluid drain containers 140 and associated tubing of disposable set 110 are all supported by one or more load cell 50, located between scale platform 60/drain container support 70 and top plate 40/frame 20. The one or more load cell 50 is powered by and sends load cell weight signals to control unit 100. The combined weight of any remaining fresh PD fluid, any collected used PD fluid and any collected UF from the patient is accordingly monitored by the one or more load cell 50. The fluid weight that one or more load cell 50 does not see is the weight of the fluid currently residing within patient P. To calculate and meter a patient fill, therefore, control unit 100 fills through valve 106a until a specified decrease in weight is recorded via one or more load cell 50. Once the desired fill weight is recorded, control unit 100 closes valve 106a. To calculate and meter a patient drain (including spent PD fluid and UF), control unit 100 drains through valve 106b and records an increase in weight via one or more load cell 50 until the patient drain has been completed, which may or may not be a specified increase in weight due, at least in part, to varying amount of UF that may be produced. Once the patient drain has been completed, e.g., via automatic determination or manual observation of a slowing in an increase of effluent weight by load cells 50, control unit 100 closes valve 106b.

The above-described configuration for suspending fresh PD fluid supply containers 144 and used PD fluid drain containers 140 of system 10 is advantageous for a number of reasons. First, as discussed, all non-patient fluid weight is sensed by the same one or more load cell 50, which streamlines load cell placement and fluid weight calculation. Second, the load cell and plate-on-plate or platform configuration via top plate 40, load cells 50 and scale platform 60 enables the output of load cells 50 to be evaluated. Load cells 50 in one embodiment are each spaced equally or approximately equally from an expected center of mass of scale platform 60 and the total weight that the platform supports, so that in theory each sense the same weight. Control unit 100 sums the weight from each of load cells 50 to arrive at a total weight sensed. For example, if the total weight sensed is 60 kilograms ("kg"), each load cell should read about 15 kg. Control unit 100 may be programmed such that if one of the load cells is consistently reading differently than the other load cells, e.g., by plus or minus ten percent, control unit sends an alert to user interface 102, and perhaps additionally or alternatively over a network to a servicing hub, server and/or portal to schedule the deviating load cell for service or replacement. The provision of multiple load cells 50 accordingly results in a self-regulating type of system.

Multiple load cells 50 also allow for scale platform 60 to read accurately even if it becomes tilted from its intended position and for self-diagnosis when tilting occurs. Upon tilting, the readings from the multiple, e.g., four, load cells should still add accurately to the total weight, but here two load cells 50 may read consistently with each other but collectively different from the other two load cells 50. For example, assume the total weight again of 60 kg, two of the load cells may read 16 kg, while the other two load cells may read 14 kg. In this tilting example, control unit 100 may be programmed to recognize that scale platform 60 is tilted from its intended position and to send an alert to user interface 102 to have the user fix the tilting issue once all bags are removed from system 10.

Regarding patient fills and drains, during treatment, the patient is typically sitting or sleeping between the upper fresh PD fluid supply container(s) and the lower used PD fluid drain container(s), so that fresh PD fluid may gravity flow from the fresh container(s) to the patient, and from the patient to the used PD fluid drain container(s). If the patient during treatment is sitting or sleeping below drain container valve 106*b*, however, then system 10 uses a siphon technique to enable the used PD fluid to flow up through drain valve 106*b* and then down the drain line to the used PD fluid drain container(s). To do so, control unit 100 prior to treatment performs a priming procedure that flows fresh PD fluid from the fresh PD fluid container(s) to vent air from the supply line and the patient line, which may be provided with a vented cap, and at least a portion of the drain line extending to and/or past drain valve 106*b*. The primed disposable set 110 enables siphoning to occur.

FIGS. 5 and 6 illustrate that control unit 100 also includes electronics 108. Electronics 108 may include any one or more of an on/off switch, an AC power plug and/or cord, one or more converter (e.g., including one or more transformer), which may for example provide electrical isolation, and a data input/output port. The electronics may also include an Ethernet card or other device allowing control unit 100 to access remote servers, e.g., via an internet or other wide area network. Control unit 100 may be programmed to receive device programs from the remote servers. The device programs may run the automated peritoneal dialysis ("APD") and the device-assisted continuous ambulatory peritoneal dialysis ("DA-CAPD") treatments described below.

Figure 4:
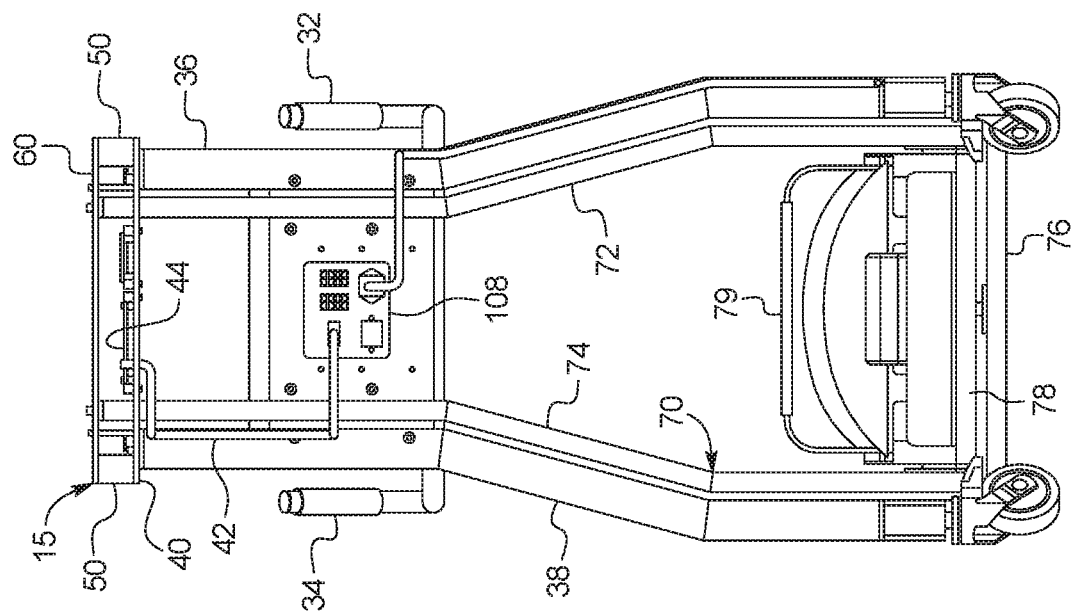
FIG. 4 is a top, rear perspective view of the gravity fed dialysis machine embodiment of FIG. 2.

FIGS. 4 and 5 illustrate that machine 15 includes an electrical/signal cable 42 extending from printed circuit boards 44 to control unit 100. Printed circuit boards 44 and cable 42 bring power to load cells 50 and include conductors configured to carry one or more different types of signals to and from control unit 100, such as first conductors carrying weight signals from the load cells 50, second conductors carrying temperature signals from thermocouples or thermistors located for example along the underside of top wall 64*b*, and/or other conductors carrying other types of sensor signals, e.g., one or more wetness or conductivity sensor poistioned in supply container receiving tray 80 to look for a leaking supply bag 140.

Figure 7B:
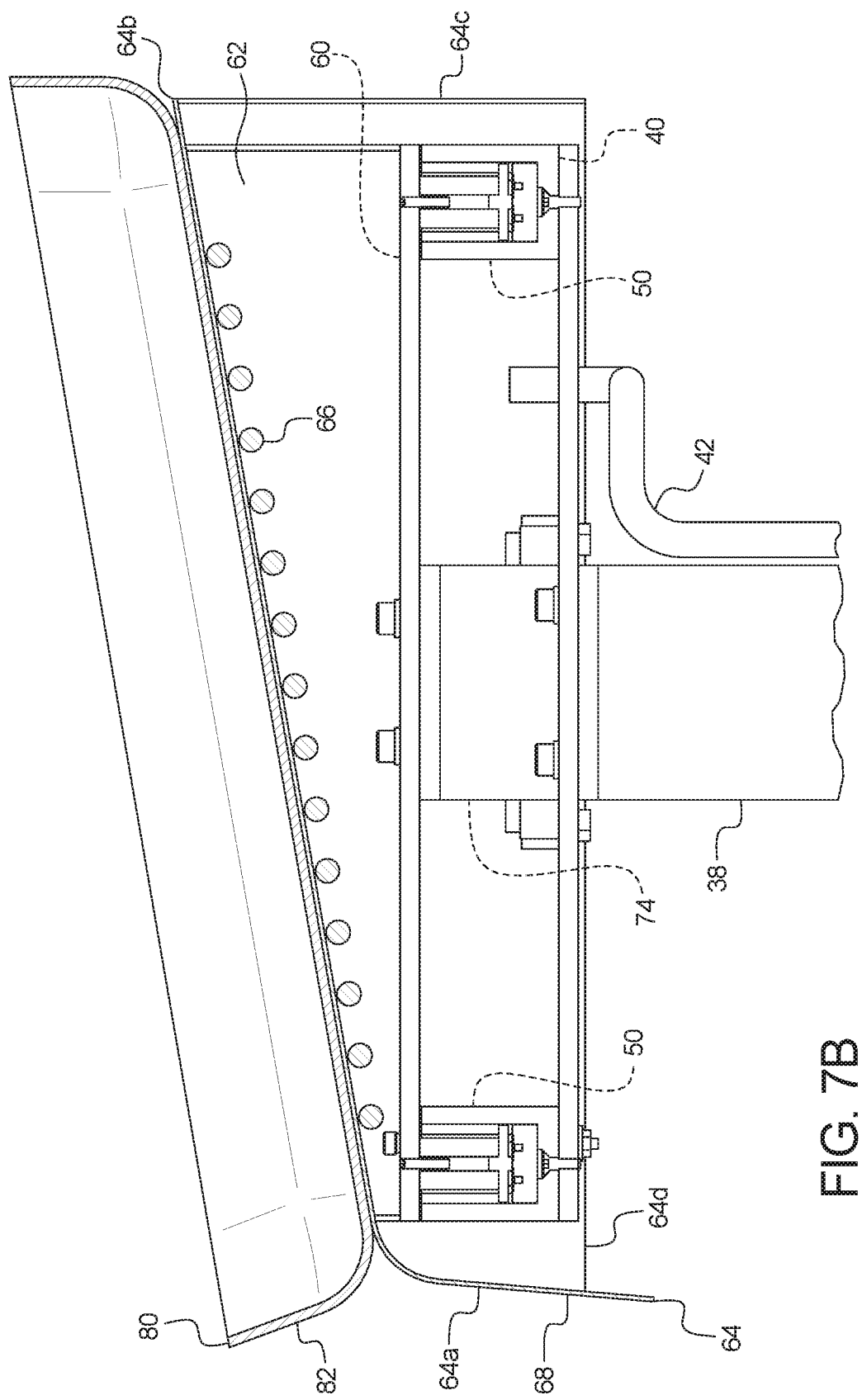
FIG. 7B is a side elevation section view of one embodiment for a load cell arrangement useable with the gravity fed dialysis machine of FIGS. 2 to 5.

FIGS. 7A and 7B illustrate top plate 40, load cells 50 and scale platform 60 in more detail. Legs 36 and 38 of frame 20 in the illustrated embodiment are bolted to top plate 40, while members 72 and 74 in the illustrated embodiment are bolted to scale platform 60. FIG. 7A illustrates, e.g., four load cells 50 located between top plate 40 and scale platform 60. FIG. 7A also illustrates printed circuit boards 44 operating with load cells 50 in more detail. FIG. 7A additionally illustrates that top plate 40 may be fitted with pins or bolts 46 that extend through mating apertures 68 formed in scale platform 60 to center the platform with respect to top plate 40, further restricting lateral movement of scale platform 60 relative to top plate 40, while allowing the scale platform to move vertically with respect to the top plate.

FIG. 7B illustrates that load cells 50 are bolted in one embodiment to top plate 40, while scale platform 60 floats on top load cells 50. FIG. 7B further illustrates that scale platform 60 may be connected to or formed with sidewalls 62, wherein the sidewalls support a cover 64. Cover 64 includes a front wall 64*a*, a top wall 64*b*, a rear wall 64*c* and side walls 64*d*. Sidewalls 62 and cover 64 float with scale platform 60. Cover 64 prevents scale platform 60 from being moved off of any load cells 50.

A supply container receiving tray 80 is provided and either rests upon or is bolted to top wall 64*b* of cover 64. Supply container receiving tray 80 is sized to receive one or more fresh PD fluid supply container of disposable set 110. In the illustrated embodiment, sidewalls 62 are angled such that top wall 64*b* of cover 64 and supply container receiving tray 80 are tilted, such that a front end of at least one fresh PD fluid supply container placed into tray 80 resides lower than a rear end of the container. The front end of the at least one container includes ports connecting to the tubing of disposable set. The tilted arrangement of the at least one fresh PD fluid supply container allows air in the container to migrate towards the elevationally raised rear end of the container(s).

In the illustrated embodiment, resistive heating coils 66 are placed within cover 64, e.g., attached to the underside of top wall 64*b* of cover 64. Heating coils 66 illustrated in cross-section in FIG. 7B may serpentine back and forth along the bottom of top wall 64*b* of cover 64. Heating coils 66 may form a single coil from an electrical standpoint or be broken into two or more coils. Heater 66 in an embodiment operates with temperature sensors (not illustrated) located along the underside of top wall 64*b* to provide temperature sensor feedback to control unit 100 to help in controlling an output of heater 66 that achieves the desired fresh PD fluid temperature. In an embdiment, electronics 44 includes analog to digital converters to fasilitate the temperature feedback. In an embodiment, control unit electronics 108 includes circuitry, e.g., sensors that sense an incoming alternating current ("AC") voltage, and switches, for example metal oxide field effect transistors ("MOSFETS"), that control unit 100 switches based on the sensed AC voltage, so that heating coils 66 receive the same heating power regardless of input AC voltage. The above-described switches and/or sensors for the heater power may be located alternatively at top plate electronics 44. Electronics 108 may also include converters that accept a range of AC input, e.g., from 90 VAC to 240 VAC, so that machine 15 may be operated regardless of AC voltage input. The converters may also output a desired voltage in a desired form, for example, convert 120 VAC to 12 VDC, depending upon the power requirements of the instruments, sensors and control unit 100 of machine 15.

Wiring (not illustrated) from heating coils 66 runs to control unit 100 via electrical/signal cable 42. Control unit 100 controls heating coils 66 to warm fresh PD fluid within its container placed on container receiving tray 80 to body temperature, e.g., 37° C. Control unit 100 may heat the fresh PD fluid using and on/off power duty cycle to coils 66. Top wall 64*b* and any one or more other walls of cover 64 (cover 64 may be a single metal piece that is bent and welded together) may be made of a thermally conductive material, such as aluminum, steel or stainless steel. Container receiving tray 80 may likewise be made of a thermally conductive material, such as aluminum, steel or stainless steel, so that heat from heating coils 66 may conduct readily to PD fluid container(s) placed on container receiving tray 80. In the illustrated embodiment, the front and side walls of container receiving tray 80 may be coated with a thermally insulated material 82 (e.g., a high melting temperature polymer, fabric, fiberglass, or perhaps a thermally insulating paint), so that a user may touch those surfaces without feeling excessive heat.

Figure 8:
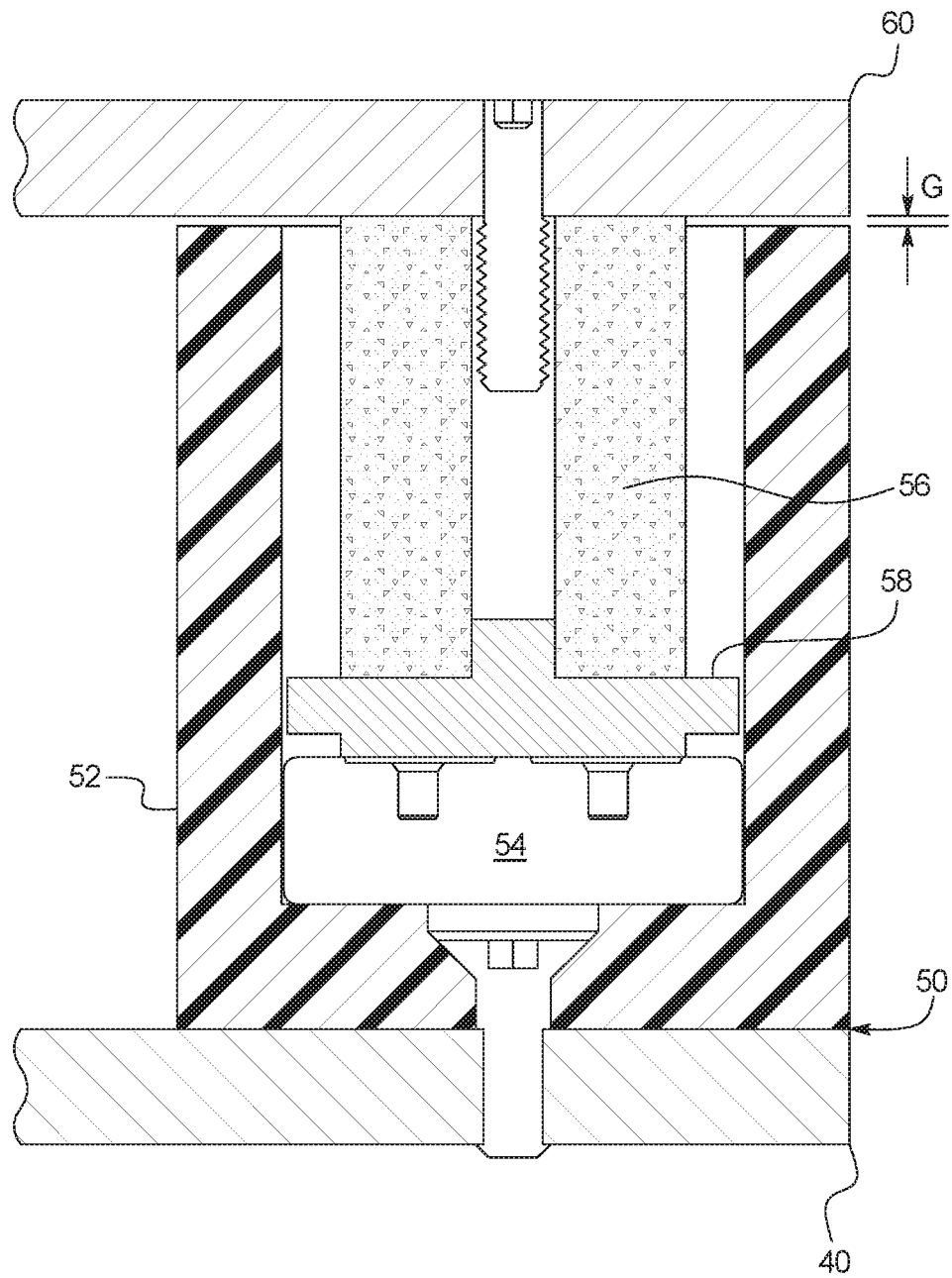
FIG. 8 is a side elevation view of one embodiment for a load cell useable with the gravity fed dialysis machine of FIGS. 2 to 5.

Referring now to FIG. 8, one embodiment for load cells 50 is illustrated. In the illustrated embodiment, load cell 50 includes a metal (e.g., stainless steel, steel, or aluminum), fiberglass or a plastic (e.g., polyethyene or polypropylene) cup 52, which aligns and secures load cell 50 to top plate 40 as illustrated. Cup 52 holds a load cell sensor 54, such that wiring (power and signal, not illustrated) of the load cell sensor 54 may extend from the cup 52 into electrical/signal cable 42 running to control unit 100.

A compressible overload bushing 56, e.g., a polyurethane compound or a compressible silicone or silicone foam, is held within cup 52 and abuts scale platform 60, as illustrated. Coil springs could be used instead of a flexible material but may be subject to excess periodic motion, which may require software filtering/dampening for correction. It should be appreciated that software filtering may be implemented regardless of the type of material (polymeric or metal) or compressible structure (compound, foam or spring) used for bushing 56. In any case, software filtering mitigates the effects of mechanical noise (vibration and other perturbations) present in system 10.

Compressible overload bushing 56 and cup 52 protect load sensor 54 from sharp changes in loading (e.g., additions due to bag placement) and from an overload of weight. Overload bushing 56 is sized and arranged to maintain a gap G between the top of cup 52 and the bottom of scale platform 60. In this manner, compressible overload bushing 56, load applicator 58 and load cell sensor 54 see the full weight placed upon (fresh PD fluid weight) and hanging from (used PD fluid weight) scale platform 60. The bushing material is selected to compress in known proportion to the application of loading, cushening the incrementally closing gap G as loads are increased through the measurement range of interest. Gap G becomes fully closed when the load has increased beyond the range of interest and approaches the overload limit of load cell sensor 54. A fully closed gap transfers all excess load to cup 52, protecting load cell sensor 54 before an overload can occur.

A metal (e.g., stainless steel, steel, or aluminum) or plastic (e.g., polyethyene or polypropylene) load applicator 58 is located beneath compressible overload bushing 56 to transfer the weight from flexible overload bushing 56 to load cell sensor 54, which in turn sends a corresponding weight signal to control unit 100. Also illustrated in FIG. 8, a screw, peg or other type of member way extend down from scale platform 60 into compressible overload bushing 56 to place platform 60 in a desired location onto load cells 50 and to prevent the platform from sliding off of load cells 50.

Disposable Set

Figure 9:
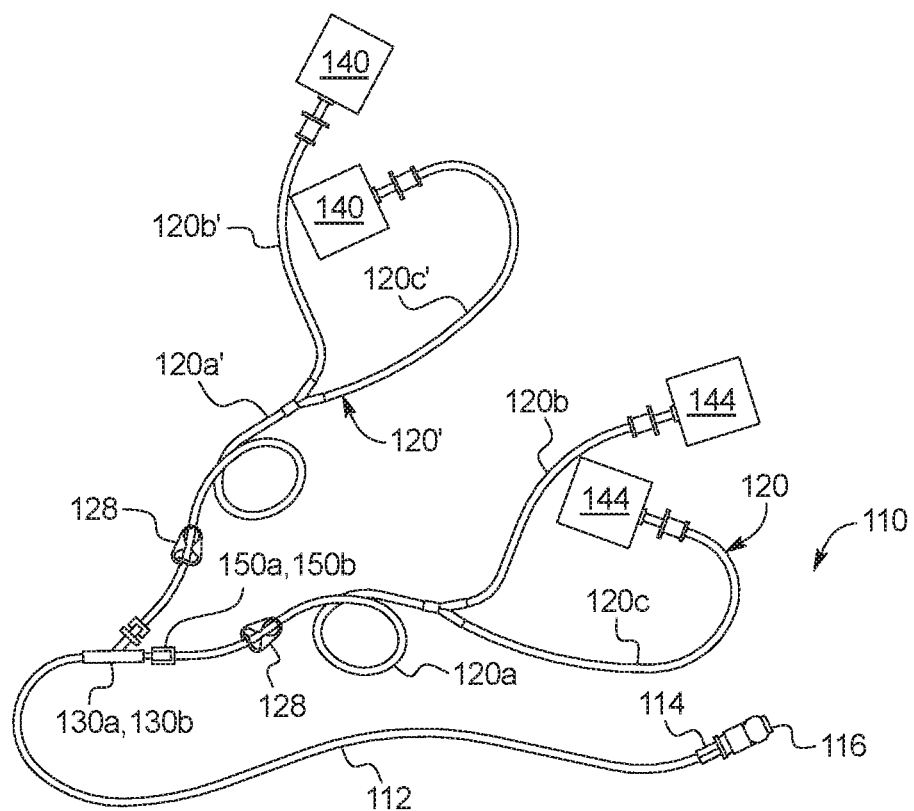
FIG. 9 is a top plan view of one embodiment of a disposable set of the present disclosure showing a fully installed set for treatment, combining a freshly opened disposable set with a reused portion of a previously used disposable set.

Referring now to FIG. 9, one embodiment of a fully connected disposable set 110 that is ready for use is illustrated. A new patient line 112 is connected to a first port of a new multi-port connector 130a or 130b (described below). A new supply line 120 is connected via branches 120b and 120c to two (or more or only a single container) full fresh PD fluid supply containers 144 (e.g., bags), and via its common section 120a to a second port of new multi-port connector 130a or 130b. Fresh PD fluid supply containers 144 are in an embodiment oversized, e.g., by ten percent or more, relative to the amount of fresh PD fluid that is held within the supply containers 144, so that supply containers 144 when used later as drain containers 140 have an extra volume to hold a patient's removed ultrafiltration ("UF") volume. Alternatively, standard sized supply containers 144 are provided typically with a certain amount of empty space filled with air, such that the standard containers may be tested to see if they are able to repeatedly hold the additional UF volume when used later as drain containers. A reused supply line 120' (now a drain line) is connected via branches 120b' and 120c' to two (or more or only a single container) empty used PD fluid drain containers 140 (e.g., bags), and via its common section 120a' to a third port of new multi-port connector 130a or 130b (described below).

After treatment, or after a twenty-four hour cycle of treatments, control unit 100 may cause any remaining fresh supply fluid to be delivered to drain containers 140, emptying PD fluid supply containers 144 so that they are ready to be reused along with supply line 120. Used PD fluid drain containers 140 are full of patient effluent (and unused fresh fluid) and are discarded along with patient line 112. It should be appreciated from FIGS. 9 to 11 that disposable set 110 reduces disposable cost and waste significantly.

Figure 10:
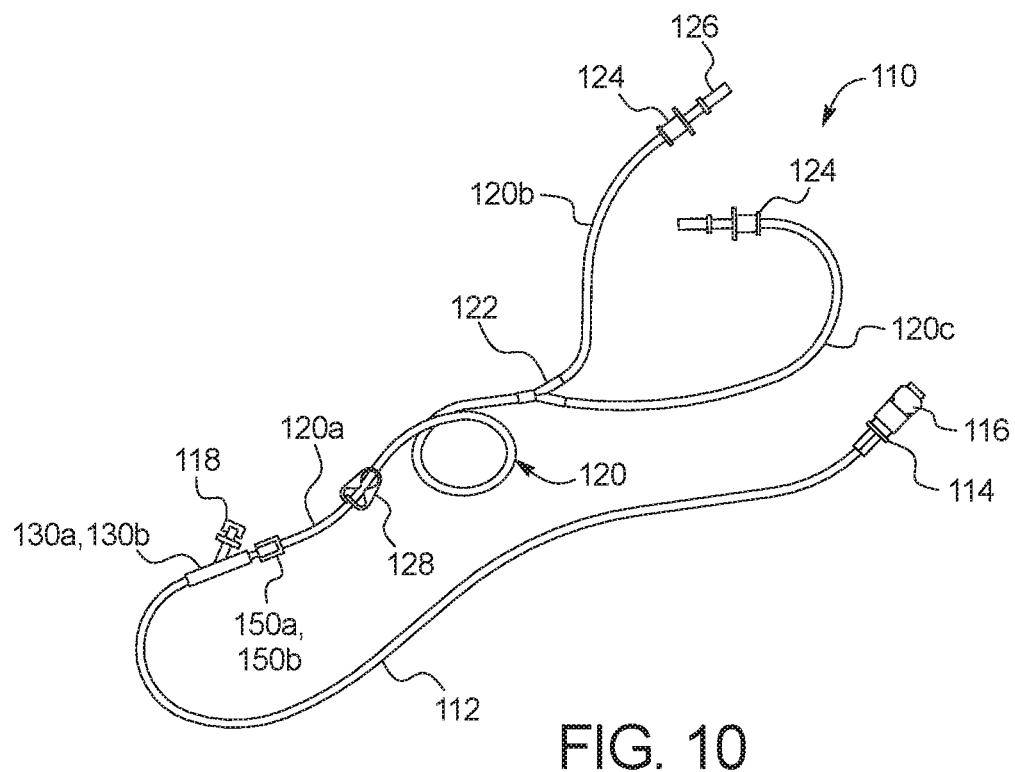
FIG. 10 is a top plan view of one embodiment of a disposable set of the present disclosure as it appears when removed from its sterile packaging.

Referring now to FIG. 10, one embodiment of disposable set 110 as packaged, or as removed from its packaging, is illustrated. Disposable set 110 is provided in a package that is sterilized via gamma radiation, steam and/or ethylene oxide. In the illustrated embodiment, disposable set 110 is not packaged with fresh PD fluid supply containers 144 or used PD fluid drain containers 140. Instead, in one embodiment, the fresh PD fluid supply containers 144 are sterilized and provided separately, while the used PD fluid drain containers 140 along with the drain line 120' are provided with the disposable set from a previous treatment. The supply lines 120 and the fresh PD fluid supply containers 144 from a present treatment are reused as drain lines 120' and used PD fluid drain containers 140 in a subsequent treatment. Reusing the supply lines 120 and the fresh PD fluid supply containers 144 from a previous treatment as drain lines 120' and used PD fluid drain containers 140 in a present treatment reduces disposable waste and cost.

The tubing of disposable set 110 may be made of a suitable medical grade material, such as polyvinylchloride ("PVC"), silicone, polypropylene ("PP"), polyethylene ("PE"), and blends thereof. The connectors of disposable set 110 may be made of a suitable medical grade material, such as PVC, silicone, PP, PE and blends thereof. The PD fluid supply containers and PD fluid drain containers of disposable set 110 may be made of a suitable medical grade material, such as the materials listed above.

FIG. 10 illustrates that disposable set 110 as packaged includes a patient line 112 that includes or is attached at a first end to a first or patient connector 114, which is configured to connect to a patient's indwelling catheter (not illustrated). The patient may for example have a patient transfer set leading to a PD catheter implanted within the patient's peritoneal cavity. Patient connector 114 is protected by a patient connector cap 116 until treatment using system 10, at which time the patient removes cap 116 and connects patient connector 114 to the patient's transfer set. Cap 116 may be fitted with a hydrophobic filter or vent to allow air to be displaced from the patient line to atmosphere during priming discussed above. Patient line 112 connects at a second end to one port of a multi-port connector 130a or 130b, such as a Y-connector or a T-connector. The connection of patient line 112 to patient connector 114 and multi-port connector 130a or 130b may be the same or different and may be any of a compression (e.g., press-fit) connection, a hose barb connection, or a luer connection. Example embodiments for multi-port connectors 130a and 130b are discussed in detail below.

FIG. 10 illustrates that disposable set 110 as packaged includes a supply line 120 having a common section 120a that branches off from a Y-connector or a T-connector 122 into a first branch 120b and a second branch 120c. Branches 120b and 120c terminate at first or supply container connectors 124, which may for example be spikes. Spikes 124 are configured to spike mating connectors of first and second PD fluid supply containers (not illustrated). Spikes 124 in the illustrated embodiment are covered by tip protectors 126. Tip protectors 126 protect spikes 124 until it is time to spike a PD fluid supply container, at which point the tip protector is removed. Connectors 124 may alternatively be compression (e.g., press-fit), hose barb or luer connectors. A line clamp 128 is placed in the illustrated embodiment at common section 120a to close or open supply line 120 as desired.

Common section 120a of supply line 120 terminates at a second or frangible connector 150a or 150b via any suitable type of connection, e.g., compression (e.g., press-fit) connection, hose barb connection, or a luer connection, and/or via bonding, such as thermal bonding, solvent bonding, ultrasonic bonding, adhesive bonding, etc. Frangible connector 150a or 150b in turn connects to a second port of multi-port connector 130a or 130b via any suitable type of connection, e.g., compression (e.g., press-fit) connection, hose barb connection, or a luer connection, and/or via bonding, such as thermal bonding, solvent bonding, ultrasonic bonding, adhesive bonding, etc. Frangible connector 150a or 150b includes a frangible portion that allows a remaining secondary connection portion to be broken off from the portion of frangible connector 150a or 150b that connects to the second port of multi-port connector 130a or 130b. The remaining secondary connection portion of frangible connector 150a or 150b is configured to seal to the third port of multi-port connector 130a or 130b via any suitable type of connection, e.g., compression (e.g., press-fit) connection, hose barb connection, or a luer connection, allowing supply line 120 and the one or more fresh PD fluid supply container 144 to serve as a drain line 120' and one or more used PD fluid drain container 140 in a subsequent treatment.

As illustrated in FIG. 10, the third port of multi-port connector 130a or 130b may be provided initially with a cap 118, wherein the cap is removable to allow supply line 120 and the secondary connection portion of frangible connector 150a or 150b from a prior dialysis treatment to be used as a drain line 120' for the present dialysis treatment, again wherein the secondary connection portion from the prior dialysis treatment is configured to removably seal to the third port of multi-port connector 130a or 130b for the dialysis treatment.

Figure 11:
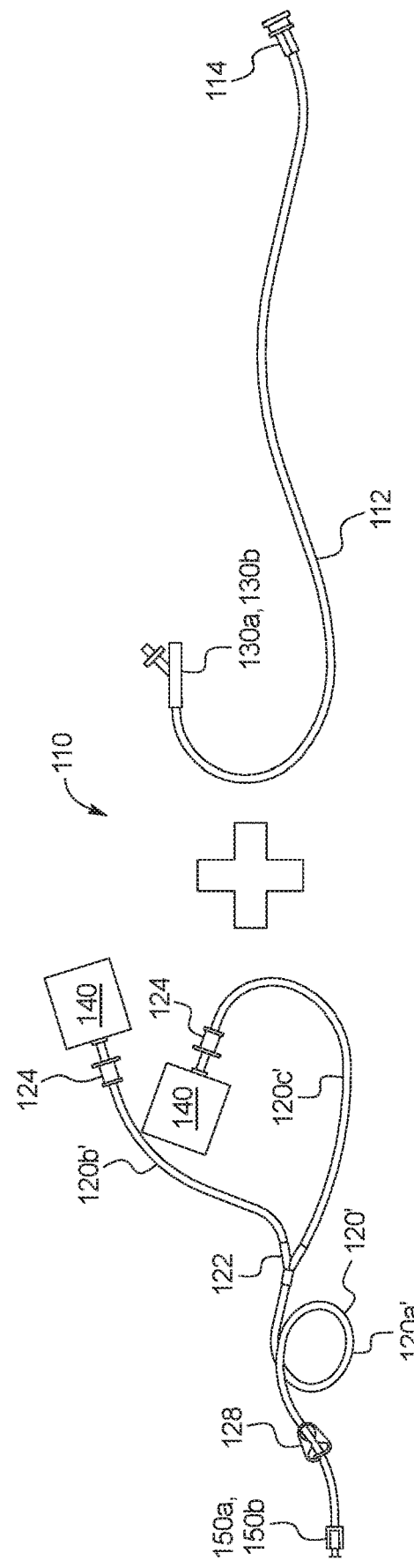
FIG. 11 is a top plan view of one embodiment of the disposable set of FIG. 10 showing which portion is used as a drain line for a subsequent treatment and which portion is discarded after treatment.

FIG. 11 illustrates disposable set 110 from FIG. 10 after use. The structure on the left of the plus sign is reused for a subsequent treatment, while the structure on the right of the plus sign is discarded. In particular, supply line 120 from FIG. 10 now becomes drain line 120' including common section 120a' connected to the remaining secondary connector 150a, 150b and branches 120b' and 120c' leading to connectors 124 connected to now empty supply bags 140 are reused, while patient line 112 leading to patient connector 114 and to multi-port connector 130a or 130b, which is connected at its second port to a small section broken off of secondary connector 150a, 150b, are discarded. Line clamp 128 may be pushed towards secondary connector 150a, 150b as far as possible before closing now drain line 120' to prevent air from entering as much of drain line 120' as possible prior to the next treatment. Closing line clamp 128 also prevents spilling of residue solution from the fresh PD fluid containers before connecting the new drain line 120' for a subsequent dialysis treatment.

Referring now to FIG. 12, an embodiment for multi-port connector 130a is illustrated. Multi-port connector 130a may be made of any of the medical grade connector materials described above. Multi-port connector 130a includes a first port 132 for connecting to patient line 112 via bonding, such as thermal bonding, solvent bonding, ultrasonic bonding, adhesive bonding, etc., compression (e.g., press-fit) connection, hose barb connection, or a luer connection. Multi-port connector 130a includes a second port 134 for connecting to supply line 120 via compression (e.g., press-fit) connection, hose barb connection, or a luer connection. Multi-port connector 130a includes a third port 136 for connecting to a reused supply line 120' via compression (e.g., press-fit) connection, hose barb connection, or a luer connection, wherein the reused supply line 120' now acts as a drain line as described above.

Third port 136 of multi-port connector 130a as illustrated includes a flange 138, which may be molded integrally with the rest of the multi-port connector. Flange 138 includes or defines multiple apertures 138a and 138b as illustrated, which are used to capture hooks from a frangible connector as discussed below FIGS. 13A and 13B illustrate an embodiment of frangible connector 150a in more detail. Frangible connector 150a is configured to connect sealingly to the third port 136 of multi-port connector 130a. Frangible connector 150a may be made of any of the medical grade connector materials described above. Frangible connector 150a includes a discarded section 152 having a port 154 that connects to the second port 134 of multi-port connector 130a via compression (e.g., press-fit) connection, hose barb connection, or a luer connection, and/or via bonding, such as thermal bonding, solvent bonding, ultrasonic bonding, adhesive bonding, etc. Frangible connector 150a also includes a remaining section 156 having a port 158 that connects to supply line 120 via compression (e.g., press-fit) connection, hose barb connection, or a luer connection, and/or via bonding, such as thermal bonding, solvent bonding, ultrasonic bonding, adhesive bonding, etc.

Discarded section 152 and remaining section 156 are separated from each other by a frangible section or line 160. The user breaks remaining section 156 and attached supply line 120 (which are reused) off of discarded section 152 and attached multi-port connector 130a and connected patient line 114 and drain line (supply line 120 from previous treatment), which are discarded. Frangible section or line 160 is configured such that its breaking force is not undue for the patient who may be elderly. Such force may be from about ten Newtons to about sixty Newtons. Remaining section 156 includes a secondary connection portion 162 that terminates at frangible line 160. Secondary connection portion 162 is sized and arranged to seal removably to third port 136 of multi-port connector 130a. For example, a largest outer diameter of secondary connection portion 162 may be 5.60 millimeters (mm), while the smallest inner diameter of third port may be 5.0 mm, causing a compression or press-fit between secondary connection portion 162 and third port 136 of multi-port connector 130a.

Remaining section 156 also includes or defines arms 164 and 166 (which may be molded integrally with frangible connector 150a) that are configured to bend, so that hooks 168 located at the distal ends of arms 164 and 166 may snap-fit into apertures 138a and 138b of third port 136 of multi-port connector 130a. The combined amount of force needed to connect secondary connection portion 162 and hooks 168 to and from third port 136 of multi-port connector 130a is selected to provide a good seal, while not being overly burdensome to a patient, who may be older. For example, the force to connect may be from about forty Newtons to about ninety Newtons (e.g., fifty Newtons), while the resulting seal force may be from about one-hundred Newtons to about two-hundred and twenty Newtons.

Figure 14A:
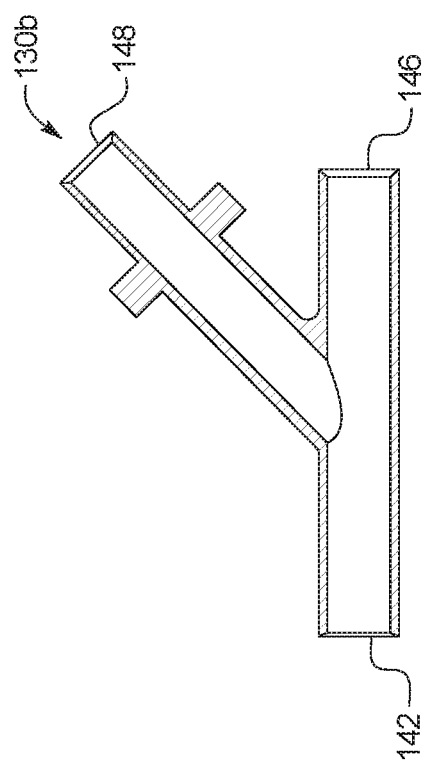
FIG. 14A is a front elevation sectional view of another embodiment of a multi-port connector used with the disposable sets of the present disclosure.
Figure 14B:
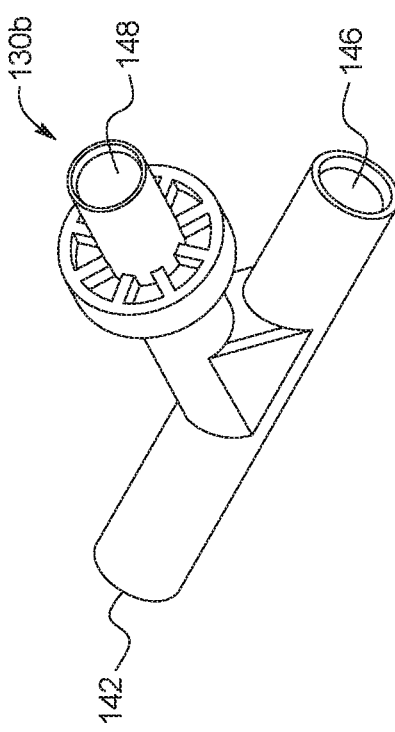
FIG. 14B is a top, front perspective view of the multi-port connector of FIG. 14A used with the disposable sets of the present disclosure.

Referring now to FIGS. 14A and 14B, an embodiment for multi-port connector 130b is illustrated. Multi-port connector 130b may be made of any of the medical grade connector materials described above. Multi-port connector 130b includes a first port 142 for connecting to patient line 112 via compression (e.g., press-fit) connection, hose barb connection, or a luer connection, and/or via bonding, such as thermal bonding, solvent bonding, ultrasonic bonding, adhesive bonding, etc. Multi-port connector 130b includes a second port 146 for connecting to supply line 120 via compression (e.g., press-fit) connection, hose barb connection, or a luer connection, and/or via bonding, such as thermal bonding, solvent bonding, ultrasonic bonding, adhesive bonding, etc. Multi-port connector 130b includes a third port 148 for connecting to a reused supply line 120' via compression (e.g., press-fit) connection, hose barb connection, or a luer connection, with reused supply line 120' now acting as a drain line as described above. Third port 148 of multi-port connector 130b as illustrated includes a flange, which may be molded integrally with the rest of the multi-port connector. Flange is used for manual manipulation of multi-port connector 130b and not for attachment to Frangible connector 150b as is the case with multi-port connector 130a and frangible connector 150a.

Figure 15B:
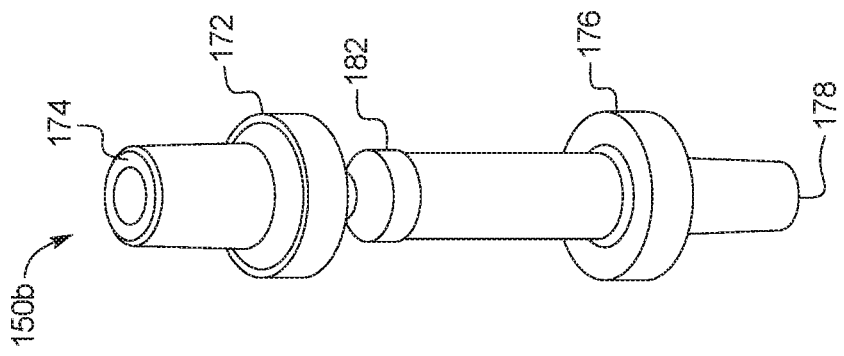
FIG. 15B is a top, front perspective view of the frangible connector of FIG. 15A used with the multi-port connector of FIGS. 14A and 14B.
Figure 15A:
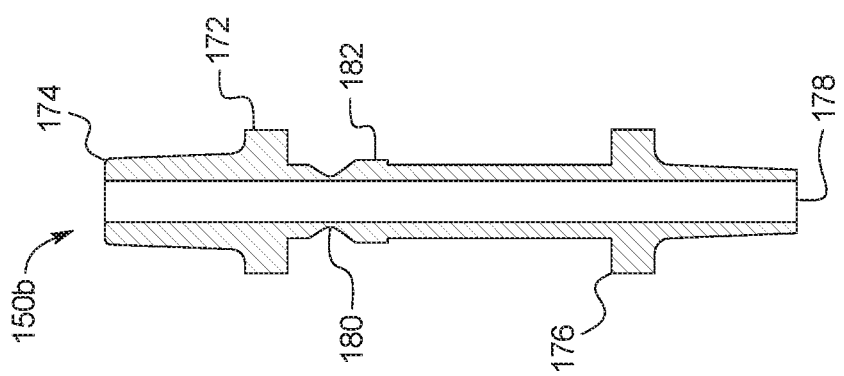
FIG. 15A is a front sectional view of one embodiment of a frangible connector used with the multi-port connector of FIGS. 14A and 14B.

FIGS. 15A and 15B illustrate an embodiment of frangible connector 150b in more detail. Frangible connector 150b is configured to connect sealingly to the third port 148 of multi-port connector 130b. Frangible connector 150b may be made of any of the medical grade connector materials described above. Frangible connector 150b includes a discarded section 172 having a port 174 that connects to the second port 146 of multi-port connector 130b via compression (e.g., press-fit) connection, hose barb connection, or a luer connection and/or via bonding, such as thermal bonding, solvent bonding, ultrasonic bonding, adhesive bonding, etc. Frangible connector 150b also includes a remaining section 176 having a port 178 that connects to supply line 120 via compression (e.g., press-fit) connection, hose barb connection, or a luer connection, and/or via bonding, such as thermal bonding, solvent bonding, ultrasonic bonding, adhesive bonding, etc.

Discarded section 172 and remaining section 176 are separated from each other by a frangible section or line 180. The user breaks remaining section 176 and attached supply line 120 (which are reused) off of discarded section 172 and attached multi-port connector 130b and connected patient line 114 and drain line (supply line 120 from previous treatment), which are discarded. Frangible section or line 180 is configured such that its breaking force is not undue for the patient who may be elderly. Such force may be from about ten Newtons to about sixty Newtons. The remaining section 176 includes a secondary connection portion 182 that terminates at frangible line 180. Secondary connection portion 182 is sized and arranged to seal removably to third port 148 of multi-port connector 130b. For example, a largest outer diameter of secondary connection portion 182 may be 6.00 millimeters (mm), while the smallest inner diameter of third port 148 may again be 5.0 mm, causing a compression or press-fit between secondary connection portion 162 and third port 148 of multi-port connector 130b.

Frangible connector 150b does not include arms as is done with frangible connector 150a to provide extra connection. Instead, the largest outer diameter of secondary connection portion 182 is made to be larger than that of secondary connection portion 182 of frangible connector 150a. The amount of force needed to connect secondary connection portion 182 to third port 148 of multi-port connector 130b may nevertheless be the same as or similar to that for secondary connection portion 162 and third port 136 of multi-port connector 130a, for example, from about forty Newtons to about ninety Newtons, e.g., fifty Newtons.

PD Treatments

System 10 performs automated patient fills, dwells and drains for the patient. It is contemplated for control unit 100 of gravity fed dialysis machine 15 to store treatments that the patient may recall and/or store a template allowing the patient to build or form a treatment for the given day. In either instance, it is contemplated to provide the patient with a choice to perform either an automated peritoneal dialysis ("APD") treatment or a device-assisted continuous ambulatory peritoneal dialysis ("DA-CAPD") treatment. The primary differences between APD treatments and DA-CAPD treatments are that (i) there are more automated cycles in APD treatments versus DA-CAPD and because of that (ii) fill volumes for APD treatments are different (typically less) than for DA-CAPD treatments, (iii) dwell times for APD treatments are different (typically less) than for DA-CAPD treatments. DA-CAPD treatments would also likely have more manual exchange steps than APD treatments, however, it is possible for an APD therapy regime to include one or more manual midday fluid exchange.

Figure 16:
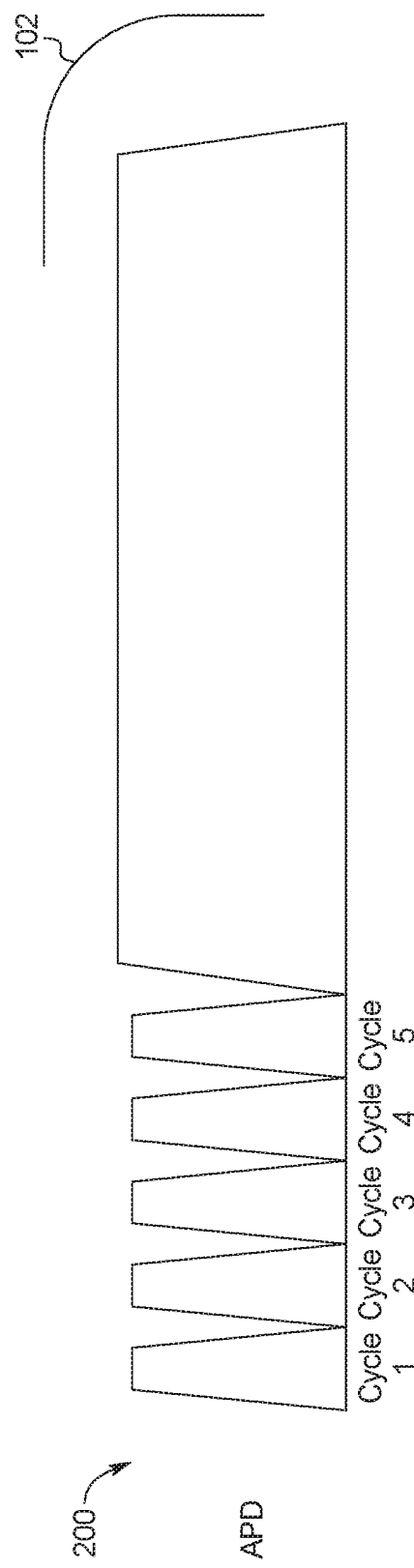
FIG. 16 illustrates an example automated peritoneal dialysis ("APD") treatment displayed on a display device of and performable by the PD system of the present disclosure.

FIG. 16 illustrates an APD treatment 200 displayed on display device 102 of machine 15. Assuming supply container receiving tray 80 holds two five liter containers of fresh dialysis fluid, the six automated fills of APD treatment 200 each may include a fill volume of about 1.6 liters. Assuming a total treatment time of nine hours, each of the five short cycles lasts about 108 minutes, which leaves a dwell time in each cycle to be one the order of 80 to 100 minutes. Machine 15 provides the last fill volume that remains with the patient during the day until the next nightly treatment with machine 15. APD treatment 200 in the illustrated embodiment has no manual exchanges.

For the three DA-CAPD examples below in FIGS. 17 to 19, the supply containers 144 of the current disposable set 110 are both empty when a new disposable set 110 is introduced, so that the supply containers may be used as drain containers with the new disposable set 110 as discussed above. Supply containers 144 may be used as drain containers for new disposable set 110 for DA-CAPD and APD. The examples below each assume that any manual fill will also use fresh dialysis fluid from the supply containers 144 located at machine 15, however, this is not required. For example, a patient's routine may include a manual drain and fill performed at work, away from machine 15. In such a case, the total fresh dialysis fluid volume loaded onto machine 15 via a new disposable set 110 may be reduced by the midday exchange volume performed at work, so that no fresh fluid is wasted.

Figure 17:
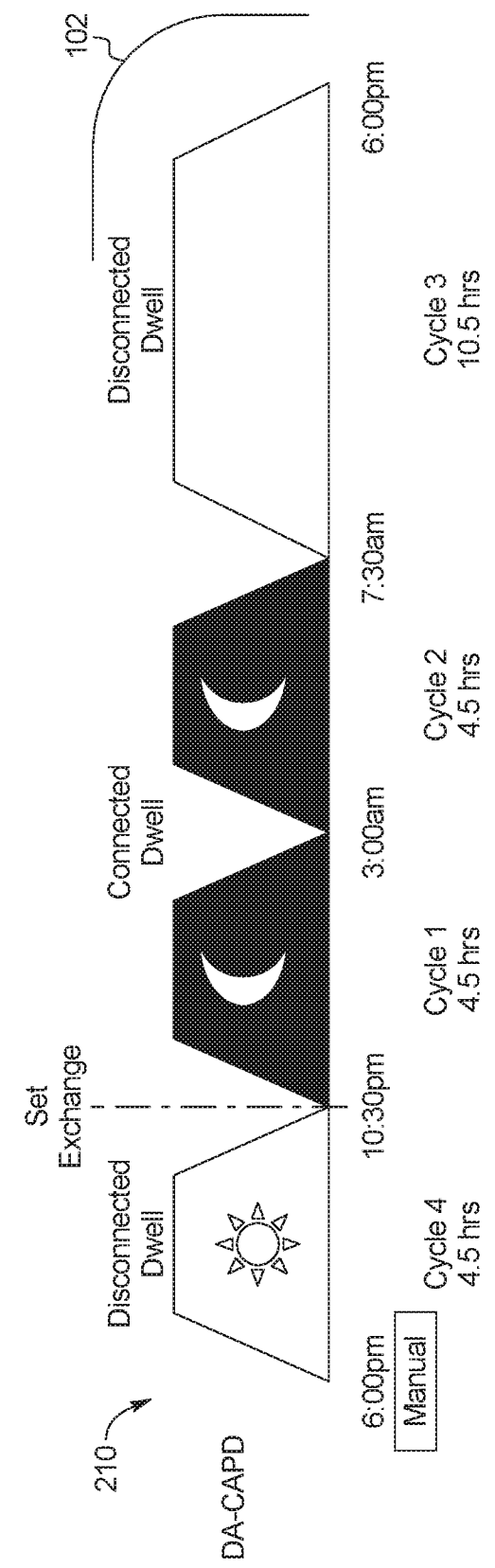
FIG. 17 illustrates a first example device-assisted continuous ambulatory peritoneal dialysis ("DA-CAPD") treatment displayed on a display device of and performable by the PD system of the present disclosure.

FIG. 17 illustrates a first DA-CAPD treatment 210 displayed on display device 102 of machine 15. Assuming supply container receiving tray 80 to again hold two five liter containers of fresh dialysis fluid, the four total cycles (three patient fills performed by machine 15) illustrated may each include a fill volume of about 2.5 liters. Assuming also a new set 110 to be loaded at the 10:30 PM exchange, the fills occurring at 10:30 PM, 3:00 AM and 7:30 AM are each performed by gravity fed PD machine 15. The automated dwells between 10:30 PM and 7:30 AM, e.g., on the order of four or more hours, are significantly longer than for APD. The drains occurring at 3:00 AM, 7:30 AM and 10:30 PM are likewise performed by gravity fed PD machine 15. The drain and fill occurring at 6:00 PM is performed manually in the illustrated embodiment, while the drain occurring at 10:30 PM may be performed manually or via machine 15. In any case, the amount of patient effort needed is reduced significantly.

FIG. 18 illustrates a second DA-CAPD treatment 220 displayed on display device 102 of machine 15. Assuming supply container receiving tray 80 to again hold two five liter containers of fresh dialysis fluid, the four total cycles illustrated may each again include a fill volume of about 2.5 liters. Assuming also a new set 110 to be loaded at the 9:00 PM exchange, the fills occurring at 9:00 PM, 1:30 AM and 6:00 AM are each performed by gravity fed PD machine 15. The automated dwells between 9:00 PM and 6:00 AM, e.g., on the order of four or more hours, are significantly longer than for APD. The drains occurring at 1:30 AM, 6:00 AM and possible 9:00 PM are likewise performed by gravity fed PD machine 15. The drain and fill occurring at 10:30 AM are performed manually in the illustrated embodiment, while the drain occurring at 9:00 PM may be performed manually or via machine 15. Nevertheless, again the amount of patient effort needed is reduced significantly.

FIG. 19 illustrates a third DA-CAPD treatment 230 displayed on display device 102 of machine 15. Assuming supply container receiving tray 80 to again hold two five liter containers of fresh dialysis fluid, the four total cycles illustrated may each again include a fill volume of about 2.5 liters. Assuming also a new set 110 to be loaded at the 11:00 PM exchange, the fills occurring at 11:00 PM, 3:00 AM and 7:00 AM are each performed by gravity fed PD machine 15. The automated dwells between 7:00 PM and 7:00 AM, e.g., on the order of 150 minutes or more, e.g., four hours or more, are longer than for APD. The drains occurring at 3:00 AM, 7:00 AM and possibly 11:00 PM are likewise performed by gravity fed PD machine 15. The drain and fill occurring at 7:00 PM are performed manually in the illustrated embodiment, while the drain occurring at 11:00 PM may be performed manually or via machine 15. Nevertheless, again the amount of patient effort needed is reduced significantly.

It should be appreciated that one main difference between APD and DA-CAPD is the dwell time. APD dwell times per cycle are usually shorter than 2.5 hours (1.5 to 2 hours typically), while DA-CAPD dwell times are usually longer than 3 hours (e.g., 4.5 hours typically). Another main difference is the total filling volume. The total fill volume (e.g., 6 to 8 liters) for DA-CAPD is lower typically than the total fill volume (e.g., 10 to 12 liters) for APD. The examples in FIGS. 17 to 19 used two five liter supply containers for DA-CAPD. The supply containers could alternatively hold three to four liters or less if the patient uses a separate supply container, e.g., at work, for a manual exchange.

Regardless of whether the treatment is an APD treatment or a DA-CAPD treatment, control unit 100 is configured to determine an amount of a patient fill by recording an instantaneous decrease in weight due to fresh PD fluid flowing from fresh PD fluid supply container(s) 144 to the patient. Control unit 100 regardless of the type of treatment also determines an amount of a patient drain by recording an instantaneous increase in weight due to used PD fluid flowing from the patient to used PD fluid drain container(s) 140. Control unit 100 may then determine an amount of ultrafiltration ("UF") removed from the patient in or both of two ways, namely, (i) calculate a UF amount after each fill, dwell and drain cycle (which may be displayed to the patient via display device 104a) and sum the UF amounts for each cycle after treatment to calculate a total UF removed for the treatment (which may also be displayed to the patient via display device 104a), or (ii) sum the fill amounts and the drain amounts after each fill, dwell and drain cycle and then subtract the total fill amount from the total drain amount at the end of treatment to determine the total UF removed for the treatment (which may also be displayed to the patient via display device 104a).

It should be appreciated that due to the load cell configuration of machine 15 as described herein, it does not matter to control unit 100 whether all fluid resides in fresh PD fluid supply container(s) 144, all fluid resides in used PD fluid drain container(s) 140, or the fluid is partitioned between supply container(s) 144 and drain container(s) 140. Control unit 100 reads the instantaneous weight from load cells 50 regardless. The differentiating weight factors are how much fluid currently resides within the patient and how much UF has been removed from the patient.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A gravity fed peritoneal dialysis ("PD") machine comprising:
   a frame configured to be set on a supporting surface;
   at least one load cell;
   a scale platform supported by the frame via the at least one load cell positioned between the frame and the scale platform; and
   a drain container support in mechanical communication with and extending downwardly from the scale platform when the frame is set on the supporting surface,
   wherein the machine is configured such that when the frame is set on the supporting surface, at least one fresh PD fluid supply container is supportable by the scale platform above the at least one load cell and at least one used PD fluid drain container is supportable by the drain container support below the at least one load cell, so that a combined weight of fresh PD fluid and used PD fluid may be sensed by the at least one load cell.

2. The dialysis machine of claim 1, wherein the drain container support includes plural members in mechanical communication with and extending downwardly from the scale platform, and a drain container receiving portion located between the plural members.

3. The dialysis machine of claim 2, which includes a drain container receiving tray removably placeable above the drain container receiving portion of the drain container support, the drain container receiving tray sized to accept the at least one used PD fluid drain container.

4. The dialysis machine of claim 2, wherein the frame includes plural legs each defining a contour, and wherein the plural members of the drain container support each define a contour matching the contour of at least one of the legs.

5. The dialysis machine of claim 1, wherein the drain container support is connected directly to the scale platform.

6. The dialysis machine of claim 1, wherein the scale platform includes plural corners, and which includes plural load cells, including one load cell supporting each corner of the scale platform, between the scale platform and the frame.

7. The dialysis machine of claim 1, which includes a supply container receiving tray in mechanical communication with the scale platform, the supply container receiving tray sized to accept the at least one fresh PD fluid supply container.

8. The dialysis machine of claim 7, wherein at least one of the scale platform or the supply container receiving tray is configured to support the at least one fresh PD fluid supply container at an angle that directs the fresh PD fluid towards a lowered outlet portion of the supply container.

9. The dialysis machine of claim 7, which includes a heater positioned and arranged to heat the supply container receiving tray to in turn the at least one fresh PD fluid supply container.

10. The dialysis machine of claim 1, which includes a control unit, a first valve under control of the control unit to selectively allow fresh PD fluid to gravity flow from the at least one fresh PD fluid supply container to a patient, and a second valve under control of the control unit to selectively allow used PD fluid to gravity flow from the patient to the at least one used PD fluid drain container.

11. The dialysis machine of claim 10, wherein the at least one load cell is in signal communication with the control unit.

12. The dialysis machine of claim 10, wherein the control unit includes a user interface, the user interface including a display and at least one input device, the control unit programmed to display a plurality of different PD treatment types and to enable a user to select one of the treatment types for an upcoming treatment using the at least one input device.

13. The dialysis machine of claim 12, wherein a first one of the PD treatment types includes automated peritoneal dialysis and a second one of the PD treatment types includes device-assisted continuous ambulatory peritoneal dialysis.

14. The dialysis machine of claim 1, wherein the at least one load cell includes a load cell mounting cup supporting a load cell sensor, the load cell mounting cup mounted to the frame and housing a load applicator positioned and arranged to deliver a load to the load cell sensor, the load applicator in mechanical communication with the scale platform.

15. A gravity fed peritoneal dialysis ("PD") machine comprising:
   a frame configured to be set on a supporting surface;
   at least one load cell;
   a scale platform supported by the frame via the at least one load cell positioned between the frame and the scale platform;
   a drain container support in mechanical communication with and extending downwardly from the scale platform when the frame is set on the supporting surface, wherein the machine is configured such that when the frame is set on the supporting surface, at least one fresh PD fluid supply container is supportable by the scale platform above the at least one load cell and at least one used PD fluid drain container is supportable by the drain container support below the at least one load cell; and
   a control unit configured to monitor an instantaneous combined weight of fresh PD fluid and used PD fluid via feedback from the at least one load cell, wherein the control unit is configured to determine an amount of a patient fill of fresh PD fluid by recording a decrease in the instantaneous combined weight, and the control unit is configured to determine an amount of a patient drain of used PD fluid by recoding an increase in the instantaneous combined weight.

16. The gravity fed PD machine of claim 15, wherein the control unit is further configured to determine an amount of ultrafiltration removed from a patient by differentiating the amount of the patient fill from the amount of the patient drain.

17. The gravity fed PD machine of claim 16, wherein the differentiating occurs (i) after multiple patient drains and summing the resulting amounts of the ultrafiltration removed or (ii) once after summing multiple patient fill amounts and patient drain amounts.

18. A peritoneal dialysis ("PD") system comprising:
   a disposable set including at least one fresh PD fluid supply container, at least one used PD fluid drain container and tubing located between the at least one fresh PD fluid supply container and the at least one used PD fluid drain container; and
   a gravity fed PD machine operable with the disposable set, the gravity fed PD machine including
   a frame configured to be set on a supporting surface,
   at least one load cell,
   a scale platform supported by the frame via the at least one load cell positioned between the frame and the scale platform, and
   a drain container support in mechanical communication with and extending downwardly from the scale platform when the frame is set on the supporting surface,
   wherein the machine is configured such that when the frame is set on the supporting surface, the at least one fresh PD fluid supply container is supportable by the scale platform above the at least one load cell and the at least one used PD fluid drain container is supportable by the drain container support below the at least one load cell, so that a combined weight of fresh PD fluid and used PD fluid may be sensed by the at least one load cell.

19. The PD system of claim 18, wherein the gravity fed PD machine includes at least one valve configured to operate with the tubing located between the at least one fresh PD fluid supply container and the at least one used PD fluid drain container.

* * * * *